United States Patent
Xie et al.

(10) Patent No.: US 11,738,116 B2
(45) Date of Patent: *Aug. 29, 2023

(54) EXPANDED NANOFIBER STRUCTURES COMPRISING ELECTROSPUN NANOFIBERS AND A PLURALITY OF HOLES AND METHODS OF MAKING AND USE THEREOF

(71) Applicant: BOARD OF REGENTS OF THE UNIVERSITY OF NEBRASKA, Lincoln, NE (US)

(72) Inventors: Jingwei Xie, Omaha, NE (US); Shixuan Chen, Omaha, NE (US); Mark Carlson, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 739 days.

This patent is subject to a terminal disclaimer.

(21) Appl. No.: 16/611,415

(22) PCT Filed: Jun. 8, 2018

(86) PCT No.: PCT/US2018/036647
§ 371 (c)(1),
(2) Date: Nov. 6, 2019

(87) PCT Pub. No.: WO2018/227078
PCT Pub. Date: Dec. 13, 2018

(65) Prior Publication Data
US 2020/0164107 A1      May 28, 2020

Related U.S. Application Data

(60) Provisional application No. 62/517,310, filed on Jun. 9, 2017.

(51) Int. Cl.
*A61L 27/38* (2006.01)
*A61L 2/00* (2006.01)
(Continued)

(52) U.S. Cl.
CPC ......... *A61L 27/3834* (2013.01); *A61L 2/0005* (2013.01); *A61L 27/222* (2013.01);
(Continued)

(58) Field of Classification Search
CPC .. A61L 27/3834; A61L 2400/12; A61L 27/54; A61L 2202/21; A61L 2300/404; A61L 2300/64; D01D 1/02
See application file for complete search history.

(56) References Cited

U.S. PATENT DOCUMENTS 6,653,005 B1    11/2003  Muradov
7,704,740 B2    4/2010   Schindler et al.
(Continued)

FOREIGN PATENT DOCUMENTS

CN    102068716 A    5/2011
CN    102071485 A    5/2011
(Continued)

OTHER PUBLICATIONS

Gu et al , Fabrication of sonicated chitosan nanofiber mat with enlarged prorosity for use as hemostatic material, Carbohydrate Polymers 97, 65-73). (Year: 2013).*
(Continued)

*Primary Examiner* — Carlos A Azpuru
(74) *Attorney, Agent, or Firm* — Robert C. Netter, Jr.; Dann, Dorfman, Herrell & Skillman

(57) ABSTRACT

Expanded, nanofiber structures comprising electrospun nanofibers, a plurality of holes, and, optionally, cells are
(Continued)

provided. Methods of making the nanofiber structures as well as methods of use thereof, particularly for wound healing, are also provided.

20 Claims, 15 Drawing Sheets

(51) Int. Cl.
| | |
|---|---|
| A61L 27/22 | (2006.01) |
| A61L 27/54 | (2006.01) |
| A61L 27/60 | (2006.01) |
| D01D 1/02 | (2006.01) |
| D01D 5/00 | (2006.01) |
| B82Y 30/00 | (2011.01) |
| B82Y 40/00 | (2011.01) |

(52) U.S. Cl.
CPC .............. *A61L 27/54* (2013.01); *A61L 27/60* (2013.01); *D01D 1/02* (2013.01); *D01D 5/003* (2013.01); *A61L 2202/21* (2013.01); *A61L 2300/232* (2013.01); *A61L 2300/64* (2013.01); *A61L 2300/802* (2013.01); *A61L 2400/12* (2013.01); *B82Y 30/00* (2013.01); *B82Y 40/00* (2013.01)

(56) References Cited

U.S. PATENT DOCUMENTS

| | | | |
|---|---|---|---|
| 9,403,958 B2 | 8/2016 | Lindner et al. | |
| 9,655,995 B2 | 5/2017 | Xie | |
| 9,913,862 B2 | 3/2018 | Collins et al. | |
| 10,799,620 B2 | 10/2020 | Xie et al. | |
| 11,033,659 B2 | 6/2021 | Xie et al. | |
| 11,318,224 B2* | 5/2022 | Xie ................... | A61L 27/34 |
| 11,427,936 B2 | 8/2022 | Xie | |
| 2005/0084532 A1 | 4/2005 | Howdle et al. | |
| 2005/0187330 A1 | 8/2005 | Gulari et al. | |
| 2006/0002978 A1 | 1/2006 | Shea et al. | |
| 2007/0077272 A1 | 4/2007 | Li et al. | |
| 2008/0112998 A1 | 5/2008 | Wang | |
| 2010/0183699 A1* | 7/2010 | Wan .................. | A61L 27/50 |
| | | | 525/434 |
| 2011/0070151 A1 | 3/2011 | Braithwaite et al. | |
| 2011/0195123 A1 | 8/2011 | Shemi | |
| 2011/0293685 A1 | 12/2011 | Kuo et al. | |
| 2012/0040581 A1 | 2/2012 | Kim | |
| 2012/0226295 A1 | 9/2012 | Jabbari | |
| 2013/0095167 A1 | 4/2013 | Warnke | |
| 2013/0112625 A1 | 5/2013 | Bahukudumbi et al. | |
| 2014/0024760 A1 | 1/2014 | Kwon et al. | |
| 2014/0051169 A1 | 2/2014 | Ganey et al. | |
| 2016/0015792 A1 | 1/2016 | Hendricus van Pinxteren et al. | |
| 2016/0015952 A1 | 1/2016 | Omachi et al. | |
| 2016/0106548 A1 | 4/2016 | Li et al. | |
| 2016/0176714 A1 | 6/2016 | Do et al. | |
| 2017/0296703 A1 | 10/2017 | Xie et al. | |
| 2019/0209732 A1 | 7/2019 | Xie et al. | |
| 2020/0277711 A1 | 9/2020 | Xie | |
| 2021/0268154 A1 | 9/2021 | Xie et al. | |
| 2022/0226537 A1 | 7/2022 | Xie et al. | |

FOREIGN PATENT DOCUMENTS

| | | |
|---|---|---|
| CN | 102703996 A | 10/2012 |
| CN | 103382625 A | 11/2013 |
| CN | 104464712 A | 3/2015 |
| CN | 106421898 A | 2/2017 |
| CN | 106492289 A | 3/2017 |
| CN | 106563172 A | 4/2017 |
| CN | 106620881 A | 5/2017 |
| CN | 105012991 B | 1/2018 |
| EP | 1611877 A1 | 1/2006 |
| EP | 2813212 A1 | 12/2014 |
| JP | 2006-169497 A | 6/2006 |
| JP | 2007160691 A | 6/2007 |
| JP | 2007222477 A | 9/2007 |
| JP | 4656320 B2 | 3/2011 |
| KR | 101493444 B1 | 2/2015 |
| WO | 00/50104 A1 | 8/2000 |
| WO | 2006/019600 A2 | 2/2006 |
| WO | 2009/011658 A1 | 1/2009 |
| WO | 2009/088777 A1 | 7/2009 |
| WO | 2014/037651 A1 | 3/2014 |
| WO | 2014/191739 A1 | 12/2014 |
| WO | 2015/051042 A2 | 4/2015 |
| WO | 2016/053988 A1 * | 4/2016 |
| WO | 2018/017929 A1 | 1/2018 |
| WO | 2018/064281 A1 | 4/2018 |
| WO | 2019060393 A1 | 3/2019 |
| WO | 2019209762 A1 | 10/2019 |

OTHER PUBLICATIONS

Liu, Y., et al., "Composite vascular scaffold combining electrospun fibers and physically-crosslinked hydrogel with copper wire-induced grooves structure" J. Mech. Behav. Biomed. Mater. (2016) 61:12-25.

Nazarov, R., et al., "Porous 3-D scaffolds from regenerated silk fibroin" Biomacromolecules (2004) 5(3):718-26.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension By a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

Ma, B., et al., "Rational design of nanofiber scaffolds for orthopedic tissue repair and regeneration" Nanomedicine (2013) 8(9):1459-81.

Chen, S., et al.,. "Recent advances in electrospun nanofibers for wound healing" Nanomedicine (Lond.) (2017) 12 (11):1335-1352.

Xie, J., et al., "The differentiation of embryonic stem cells seeded on electrospun nanofibers into neural lineages" Biomaterials (2009) 30(3):354-362.

Xie, J, et al., "Controlled biomineralization of electrospun poly($\epsilon$-caprolactone) fibers for enhancing their mechanical properties" Acta Biomaterialia (2013) 9(3):5698-5707.

Dehghani, et al., "Engineering porous scaffolds using gas-based techniques" Current Opinion in Biotechnology (2011) 22:661-666.

Mulmi, et al., "Fabrication of Air Freshening Spongy Three Dimensional Electrospun Membrane" Journal of the Institute of Engineering (2018) 14(1):14-21.

Keit, et al., "Expansion of Two-dimension Electrospun Nanofiber Mats into Three-dimension Scaffolds" J. Vis. Exp. (2018):e58918.

Jiang, J., et al., "Expanded Three-dimensional Nanofiber Scaffolds: Cell Penetration, Neovascularization, and Host Response" Adv. Healthc. Mater. (2016) 5(23): 2993-3003.

Jiang, J., et al., "CO2-Expanded Nanofiber Scaffolds Maintain Activity of Encapsulated Bioactive Materials and Promote Cellular Infiltration and Positive Host Response" Acta Biomater. (2018) 68: 237-248.

(56) References Cited

OTHER PUBLICATIONS

Hwang, P.T.J., et al., "Poly(ε-caprolactone)/gelatin composite electrospun scaffolds with porous crater-like structures for tissue engineering" J Biomed Mater Res A. (2016) 104(4):1017-1029.

Liu, Y., et al., "HB-EGF embedded in PGA/PLLA scaffolds via subcritical CO2 augments the production of tissue engineered intestine" Biomaterials (2016) 103:150-159.

Borjigin, M., et al., "Proliferation of Genetically Modified Human Cells on Electrospun Nanofiber Scaffolds" Mol. Ther.-Nuc. Acids (2012) 1:e59.

Geiger, B.C., et al., "Dual drug release from CO2-infused nanofibers via hydrophobic and hydropjilic interactions" J. Appl. Polym. Sci. (2015) 132:42571.

Ayodeji, O., et al., "Carbon dioxide impregnation of electrospun polycaprolactone fibers" J. Supercritical Fluids (2007) 41:173-178.

Lee, S.J., et al., "The use of thermal treatments to enhance the mechanical properties of electrospun poly(E-caprolactone) scaffolds" Biomaterials (2008) 29:1422-1430.

Xie, J., et al., "Electrospray in the dripping mode for cell microencapsulation" J. Colloid Interface Sci. (2007) 312:247-255.

Cai, H., et al., "Aerogel Microspheres from Natural Cellulose Nanofibrils and Their Application as Cell Culture Scaffold" Biomacromolecules (2014) 15:2540-2547.

Wang, W., et al., "Dentin regeneration by stem cells of apical papilla on injectable nanofibrous microspheres and stimulated by controlled BMP-2 release" Acta Biomater. (2016) 36:63-72.

Joshi, M.K., et al., "Multi-layered macroporous three-dimensional nanofibrous scaffold via a novel gas foaming technique" Chem. Engr. J. (2015) 275:79-88.

Zhao, Y., et al., "Preparation of Nanofibers with Renewable Polymers and Their Application in Wound Dressing" Intl. J. Polmer Sci. (2016) 2016:4672839.

Pok, S., et al., "A multilayered scaffold of a chitosan and gelatin hydrogel supported by a PCL core for cardiac tissue engineering" Acta Biomater. (2013) 9(3):5630-5642.

Electrospin Tech, "Post-electrospinning expansion of 2D membrane to 3D scaffold using gas foaming" (Oct. 27, 2015) available at: http://electrospintech.com/gasfoam3d.html#.X5bnPC9h0kg.

Gao, Q., et al., "Fabrication of electrospun nanofibrous scaffolds with 3D controllable geometric shapes" Mater. Design (2018) 157:159-169.

Boda, S.K., et al., "Electrospraying Electrospun Nanofiber Segments into Injectable Microspheres for Potential Cell Delivery" ACS Appl. Mater. Interfaces (2018) 10:25069-25079.

Boda, S.K., et al., "Mineralized nanofiber segments coupled with calcium-binding BMP-2 peptides for alveolar bone regeneration" Acta Biomater. (2019) 85:282-293.

Fu, L., et al., "Three-dimensional nanofiber scaffolds with arrayed holes for engineering skin tissue constructs" MRS Communications (2017) 7:361-366.

Gu, B.K., et al., "Fabrication of sonicated chitosan nanofiber mat with enlarged porosity for use as hemostatic materials" Carbohydr. Polym. (2013) 97(1):65-73.

Wei, et al., "The multifunctional wound dressing with core-shell structured fibers prepared by coaxial electrospinning" Front. Mater. Sci. (2016) 10(2):113-121.

* cited by examiner

FIG. 9A
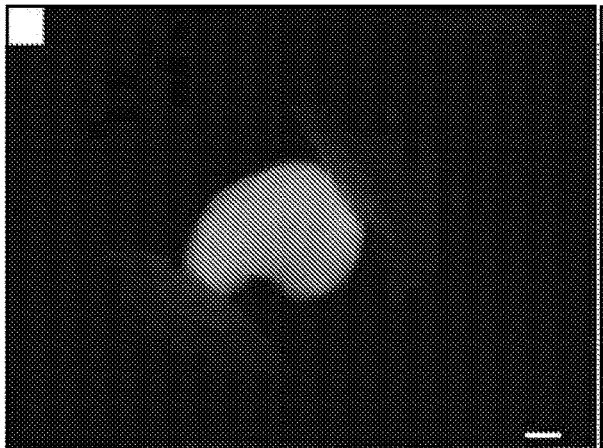
FIG. 9B
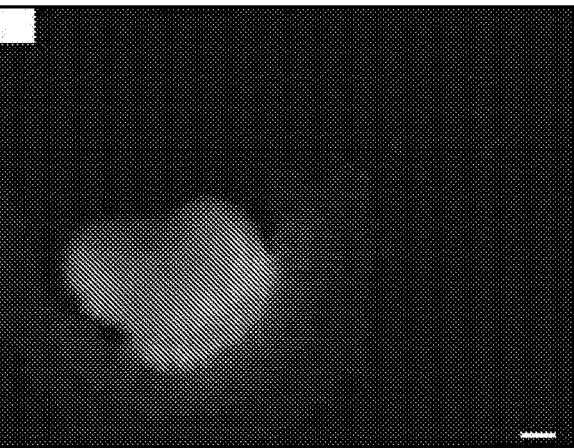
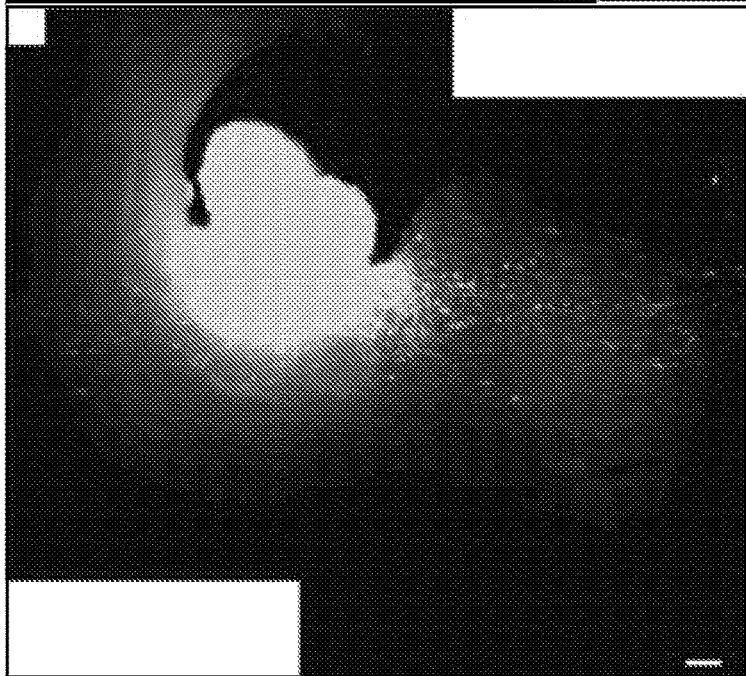
FIG. 9C

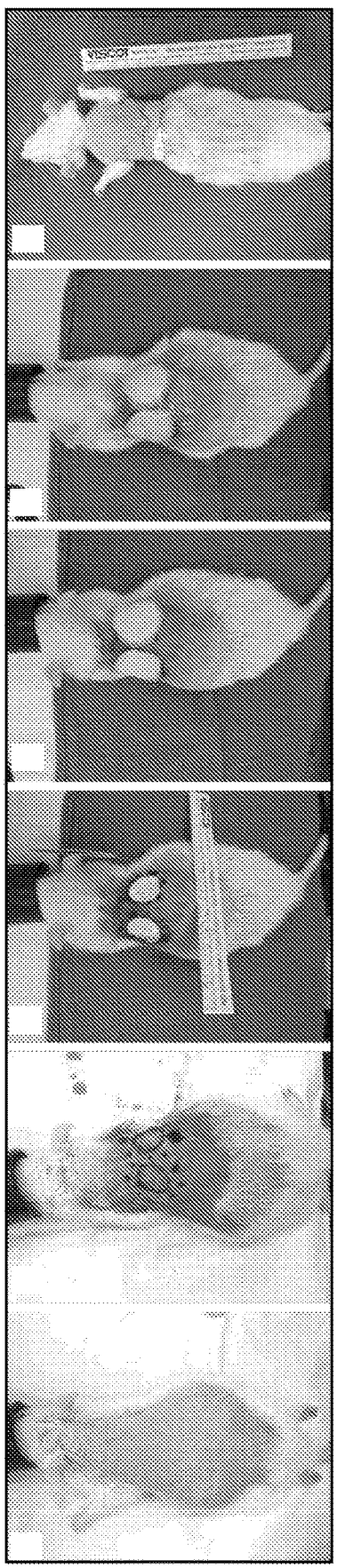
FIG. 10A
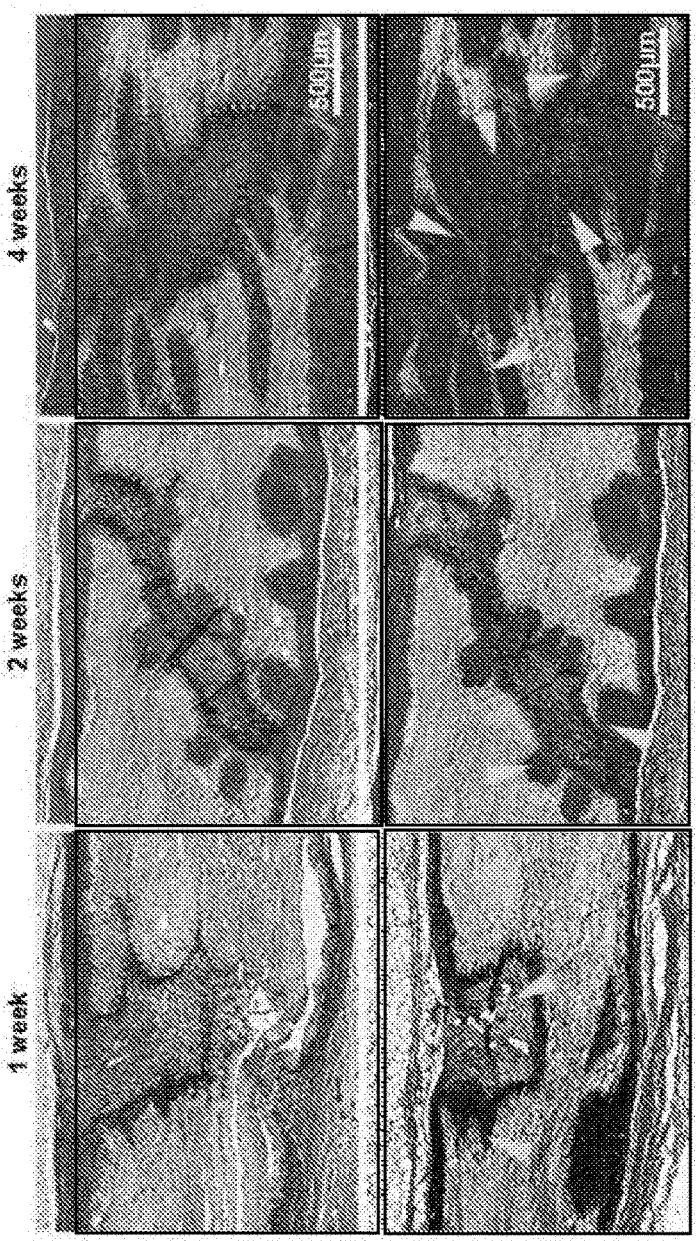
FIG. 10B
FIG. 10C

US 11,738,116 B2

EXPANDED NANOFIBER STRUCTURES COMPRISING ELECTROSPUN NANOFIBERS AND A PLURALITY OF HOLES AND METHODS OF MAKING AND USE THEREOF

This application is a § 371 application of PCT/US2018/036647, filed Jun. 8, 2018, which claims priority under 35 U.S.C. §119(e) to U.S. Provisional Patent Application No. 62/517,310, filed Jun. 9, 2017. The foregoing applications are incorporated by reference herein.

This invention was made with government support under Grant No. P20 GM103480 awarded by the National Institutes of Health (NIH). The government has certain rights in the invention.

FIELD OF THE INVENTION

This application relates to the fields of nanofibers and nanofiber structures. More specifically, this invention provides absorbent nanofiber structures and methods of use thereof, particularly with regard to wound healing.

BACKGROUND OF THE INVENTION

Several publications and patent documents are cited throughout the specification in order to describe the state of the art to which this invention pertains. Each of these citations is incorporated herein by reference as though set forth in full.

In the United States alone, chronic wounds affect 6.5 million patients and the associated cost for treating these wounds is about $25 billion each year (Sen, et al., Wound Repair Regen. (2009) 17:763-771). Timely healing and closure is critical to reducing the cost and morbidity associated with chronic lower extremity wounds (Anderson, et al., Diabet. Foot Ankle (2017) 3:10204). Debridement of the wound area and grafting with autologous split thickness grafts is still the standard for the treatment of chronic wounds (Simman, et al., J. Am. Coll. Certif. Wound Spec. (2011) 3:55-59; Hackl, et al., Plast. Reconstr. Surg. (2012) 129:443e-452e). However, the success rate of split thickness skin graft (STSG) for healing chronic wounds is low—in the range of 33-73% (Hogsberg, et al., PLoS One (2011) 6:20492e). Besides, meshed skin grafts usually require large areas of donor skin tissues for wound coverage due to their limited expansion ratios, which causes the potential risks of donor site morbidity and poor wound healing unique to the diabetic state (McCartan, et al., Plastic Surg. Int. (2012) 2012:715273). Microskin grafts (e.g. autograft islands, and stamp autografts) are often associated with low acceptance rates and the severe scarring (Biswas, et al., J. Diabetes Sci. and Technol. (2010) 4:808-819). In addition, the interstices of the grafts tend to form hypertrophic scarring. In view of the foregoing, it is clear that improved compositions and methods for wound healing are needed.

SUMMARY OF THE INVENTION

In accordance with the instant invention, nanofiber/nanofibrous structures are provided. In a particular embodiment, the nanofiber/nanofibrous structures comprise an expanded, nanofiber structure comprising a plurality of nanofibers. In a particular embodiment, the nanofiber structure comprises a plurality of holes, particularly an array of holes. In a particular embodiment, the holes of the nanofiber structure comprise cells and/or tissue. In a particular embodiment, the nanofiber structure has been expanded by exposure to gas bubbles. The gas bubbles may be generated by a chemical reaction and/or physical means. In a particular embodiment, the gas bubbles are generated as a product of a chemical reaction (e.g., the hydrolysis of sodium borohydride). The nanofiber structure may comprise a plurality of nanofibers (e.g., uniaxially-aligned, random, entangled, and/or electrospun fibers) prior to exposure to the gas bubbles. The nanofiber structure may also comprise a material that enhances water absorption, such as gelatin, chitosan, or collagen. In a particular embodiment, the nanofiber structure is crosslinked. The nanofiber structure may also comprise one or more agents or compounds such as therapeutic agents. Methods of synthesizing the nanofiber structure are also provided.

In accordance with another aspect of the instant invention, methods of using the nanofiber structures are provided. For example, the nanofiber structures may be used to enhance wound healing, tissue engineering, and/or promote tissue regeneration.

BRIEF DESCRIPTION OF THE DRAWINGS

FIG. 1A: Nanofiber membrane generated by electrospinning. FIG. 1B: Punch arrayed holes throughout nanofiber membranes and expansion of the membrane in the third dimension using the modified gas-foaming method. FIG. 1C: Seed minced skin tissues to the arrayed holes to form nanofiber skin grafts ready for implantation to the chronic wound. FIG. 1D: After implantation, cells migrated from minced skin tissues to the surrounding areas to form 3D tissue constructs and heal the chronic wound.

FIG. 3A: Electrospinning parameters: solution=5% PCL/gelatin (50:50) in HFIP, flow rate=0.4 mL/hour, high voltage=18 kV, distance between collector (drum) and needle=21 cm, rotating speed=1340 rpm. FIG. 3B: FFT analysis of random PCL/gelatin fibers in FIG. 3A. FIG. 3C: Electrospinning parameters: solution=5% PCL/gelatin (50:50) in HFIP, flow rate=0.4 mL/hour, high voltage=18 kV, distance between collector (drum) and needle=21 cm, rotating speed=7348 rpm. FIG. 3D: FFT analysis of aligned PCL/gelatin fibers in FIG. 3C.

FIGS. 4A, 4D: Non-crosslinked fibers before (FIG. 4A) and after (FIG. 4D) water treatment. FIGS. 4B, 4C, 4E, and 4F: Crosslinked fibers before (FIGS. 4B, 4C) and after (FIGS. 4E, 4F) water treatment. Scale bar=10 µm. Electrospinning parameters: solution=5% PCL/gelatin (50:50) in HFIP, flow rate=0.4 mL/hour, voltage=18 kV, distance between collector (aluminum foil) and needle=22 cm.

FIG. 7A provides a photograph of a 3D nanofiber scaffold with around 5 mm thick and arrayed holes. Scale bar=5 mm. FIG. 7B provides an image of the punched hole. Scale bar=200 µm. FIG. 7C provides a corresponding highly magnified image of FIG. 7B showing layered structures. Scale bar=50 µm. FIG. 7D provides an image of cross sections of the edge of 3D scaffolds. Scale bar=100 µm. FIG. 7E provides images of cross sections of the middle of 3D scaffolds. Scale bar=100 µm. FIG. 7F provides a corresponding highly magnified image of FIG. 7E showing nanofiber layers after expansion. Scale bar=10 µm. The nanofibers were fabricated by electrospinning 5% PCL/gelatin (50:50) in HFIP. Electrospinning parameters: flow rate=0.4 mL/hour, voltage=18 kV, the distance between the collector (drum) and needle=21 cm.

FIGS. 9A-9C provide images of GFP-HDF spheroid-seeded 3D PCL/gelatin nanofiber scaffolds after incubation for 1 (FIG. 9A), 4 (FIG. 9B), and 5 days (FIG. 9C). Scale bar=100 µm.

FIG. 10A provides images of the implantation of the PCL nanofiber scaffolds with arrayed holes in rats. FIGS. 10B-10E provide images of the in vivo response of expanded nanofiber scaffolds with punched holes. FIG. 10B: hematoxylin and eosin (H & E) staining. FIG. 10C: Masson trichrome staining. FIG. 10D: Highly magnified images of FIG. 10B showing blood vessels. FIG. 10E: Highly magnified images of FIG. 10B showing giant cells.

DETAILED DESCRIPTION OF THE INVENTION

Figure 1A:
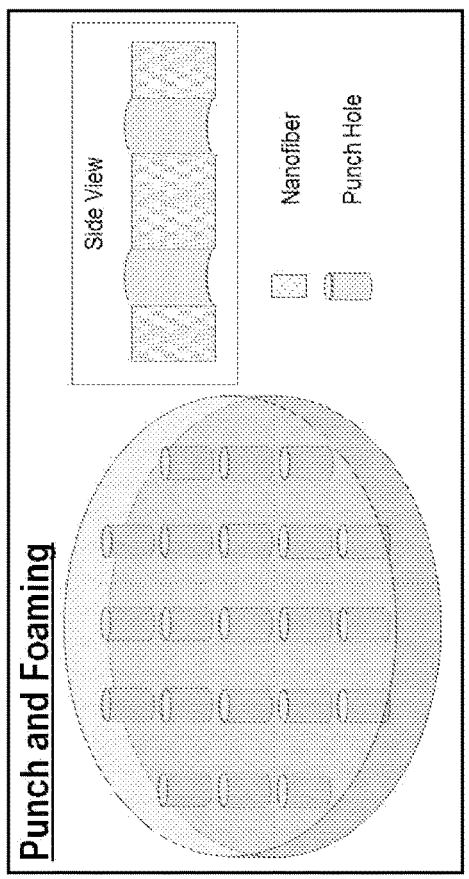
FIGS. 1A-1D provide schematics illustrating the fabrication of nanofiber skin grafts and the mechanism for chronic wound healing.
Figure 1B:
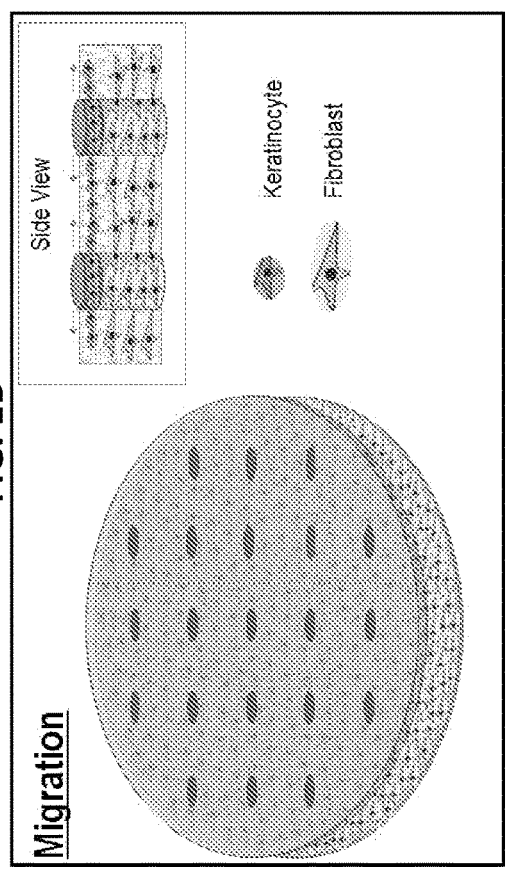
Figure 1C:
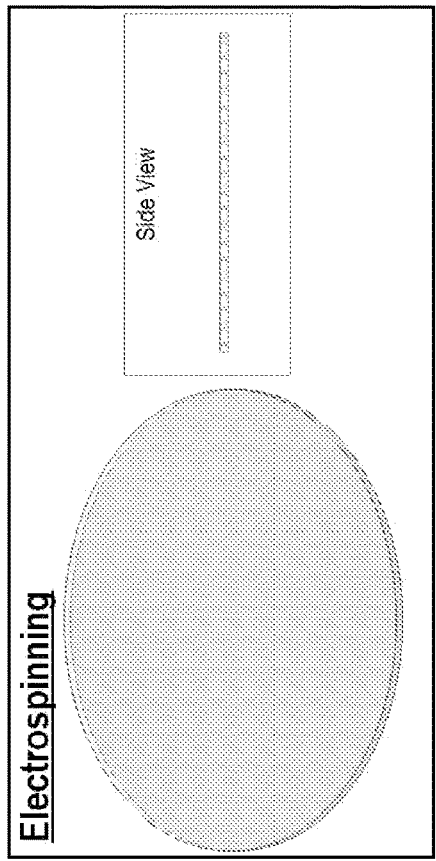
Figure 1D:
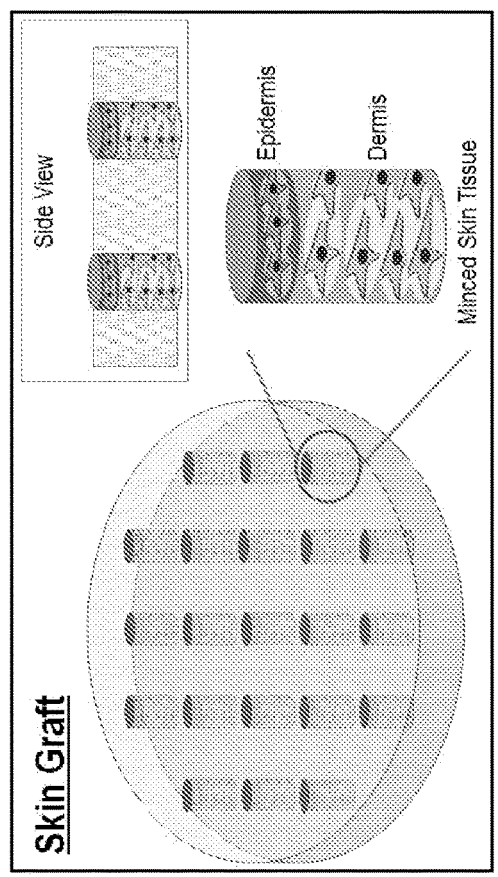
Figure 2A:
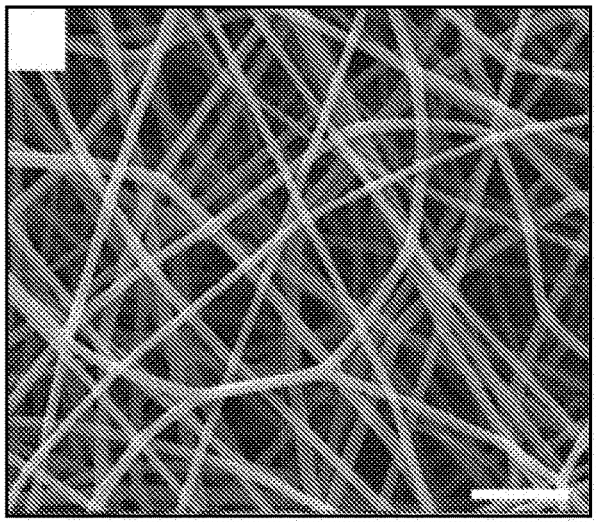
FIGS. 2A-2D provide scanning electron microscopy (SEM) images of electrospun polycaprolactone (PCL)/gelatin (50:50) fibers fabricated under different conditions. Scale bar=10 µm. The nanofibers were fabricated by electrospinning 10% (FIGS. 2A, 2C) and 5% (FIGS. 2B, 2D) PCL/gelatin (50:50) in hexafluoro-2-proponal (HFIP). Electrospinning parameters: flow rate=1.5 mL/h (FIGS. 2A, 2C) and 0.4 mL/h (FIGS. 2B, 2D), voltage=18 kV, the distance between the collector (drum) and needle=21 cm.
Figure 2B:
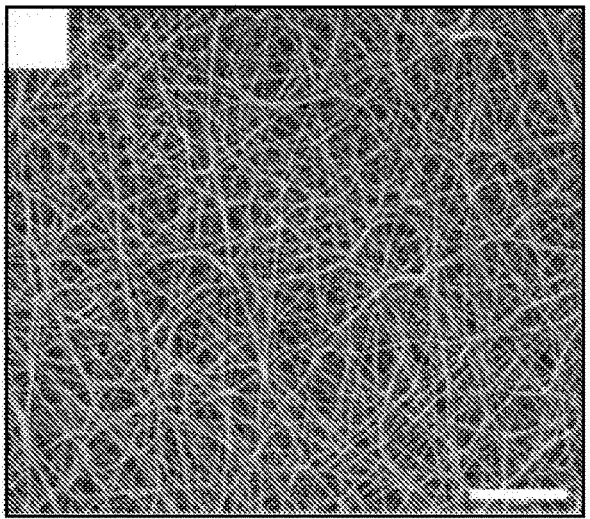
Figure 2C:
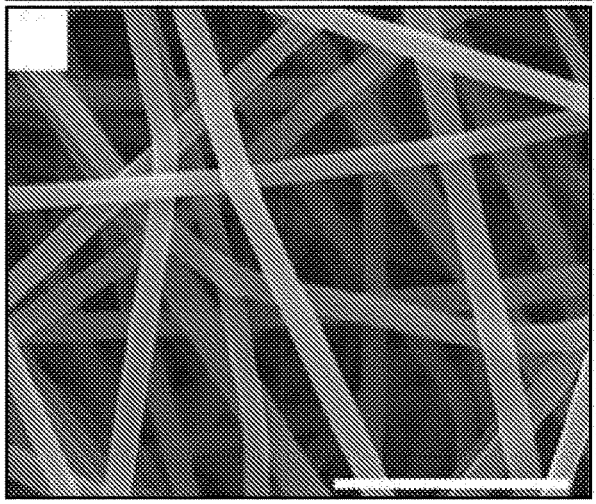
Figure 2D:
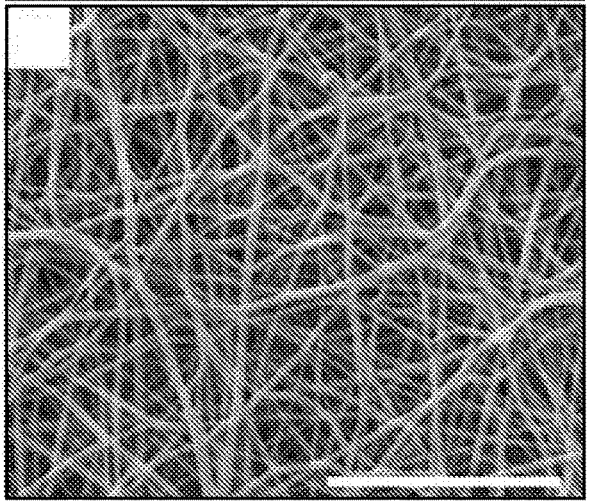
Figure 3A:
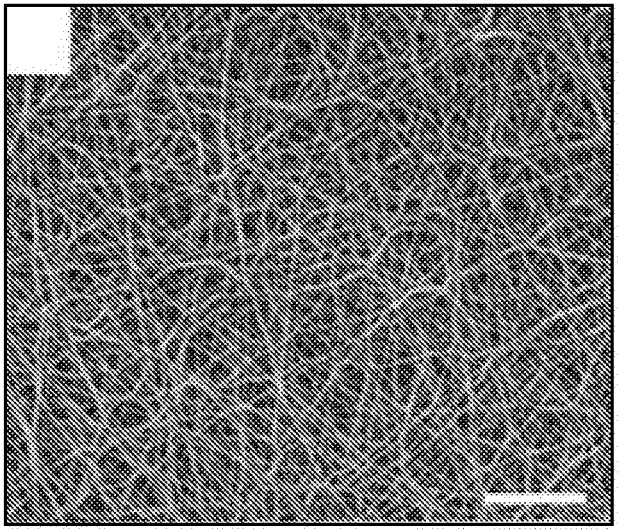
FIGS. 3A-3D provide SEM images and fast Fourier transform (FFT) analysis of random and aligned PCL/gelatin (50:50) nanofibers. Scale bar=10 µm.
Figure 3B:
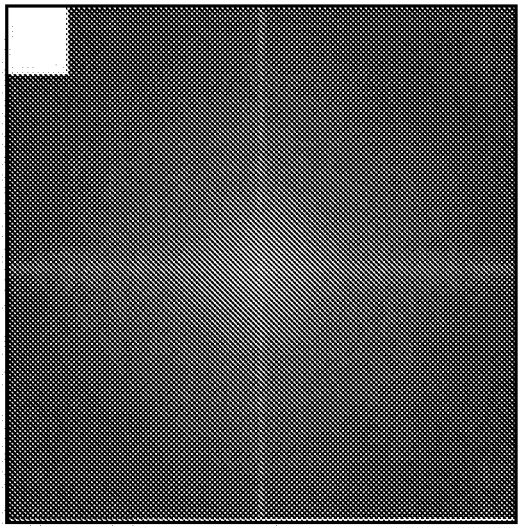
Figure 3C:
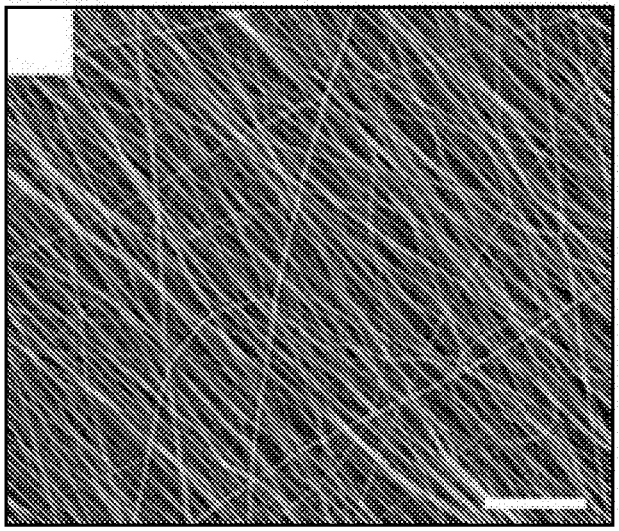
Figure 3D:
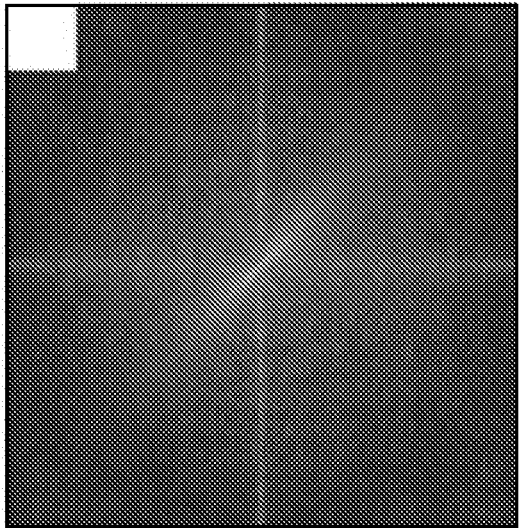
Figure 4A:
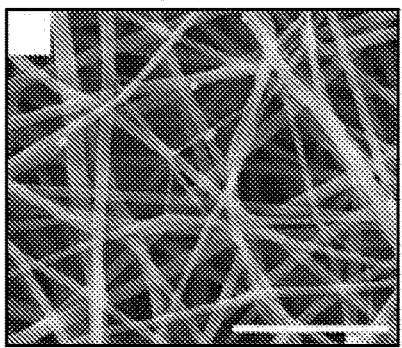
FIGS. 4A-4F provide SEM images of electrospun nanofibers before and after water treatment.
Figure 4B:
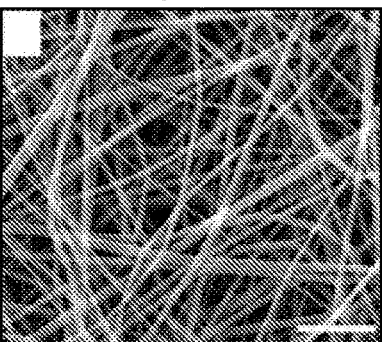
Figure 4C:
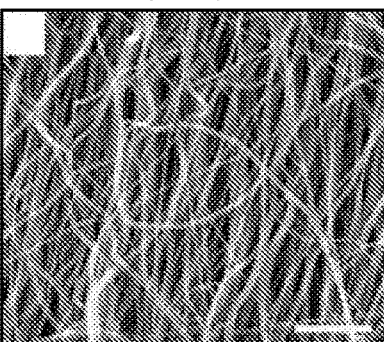
Figure 4D:
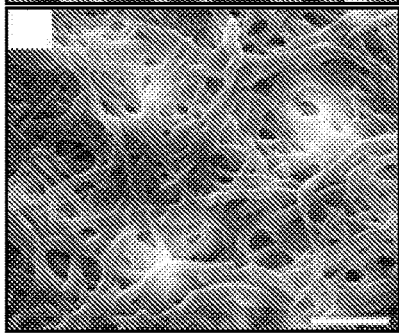
Figure 4E:
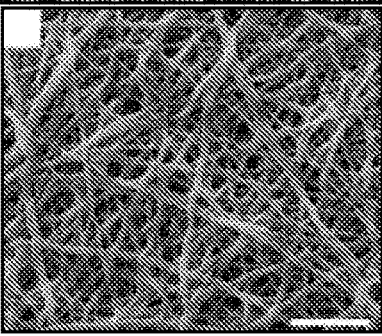
Figure 4F:
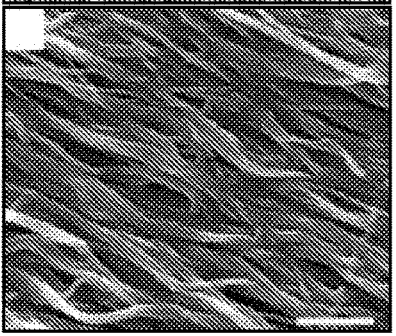

One goal of tissue engineering is to use a combination of cells/tissues, engineered materials, and suitable biochemical and physical cues to restore, maintain, or improve biological functions of damaged tissues or organs (Langer, et al., Science (1993) 260:920-926). Tissue engineered skin grafts may provide an optimized solution to improved healing of chronic wounds. The fabrication of a "sandwich-type" nanofiber-based skin graft has been demonstrated through seeding minced skin tissues onto the microwells of nanofiber membrane and covering with a radially aligned nanofiber membrane (Ma, et al., Biomaterials (2014) 35:630-641). Although nanofiber membranes were able to direct cell migration and achieve the full cell coverage on the surface of membranes in a short period of time, the nanofiber membranes used were two dimensional (2D) and cells only migrated on their surface.

Herein, a novel type nanofiber skin graft for wound healing, including chronic wound healing, is provided. Rather than use a 2D graft, a modified gas-foaming technique has been used to expand 2D nanofiber membranes in the third dimension with controlled thickness and highly porous structures (Jiang, et al., ACS Biomaterials Sci. & Eng. (2015) 1:991-1001; Jiang, et al., Adv. Healthcare Mater. (2016) 5:2993-3003; Jiang et al., Acta Biomater. (2018) 68: 237-248). More specifically, three-dimensional (3D) scaffolds composed of PCL and gelatin nanofibers were fabricated by a combination of electrospinning and modified gas-foaming. Arrayed holes throughout the scaffold were created using a punch under cryo conditions. The scaffolds were also crosslinked with glutaraldehyde vapor to improve the water stability of the scaffolds. Cell spheroids of green fluorescent protein-labeled human dermal fibroblasts (GFP-HDF) were prepared and seeded into the holes. It was found that the fibroblasts adhered well on the surface of nanofibers and migrated into the scaffolds and proliferate due to the porous structures. The 3D nanofiber scaffolds of the instant invention can be used for engineering tissue constructs or models for various applications.

Using small amount of minced skin tissues (e.g., 1 mm in diameter), the 3D nanofiber scaffolds with arrayed holes of the instant invention are able to provide the physical support and biological response to cell proliferation and infiltration. This clinically relieves the lack of autograft donor sites. Thus, the instant invention has demonstrated the development of a nanofiber skin graft by combining 3D nanofiber scaffolds with arrayed holes and cellular inserts (e.g., minced tissues (e.g., skin tissues), bone fragments) for chronic wound healing (FIG. 1). Indeed, after implantation the cells migrate out from arrayed holes to the surrounding space to heal the wound. Comparing to the typical 2D fibrous scaffolds, the 3D nanofiber scaffolds with arrayed holes of the instant invention have a highly porous 3D network which allows the cells to migrate and infiltrate through the whole scaffold.

Briefly, 2D nanofiber membranes were fabricated using electrospinning (Ma, et al., Biomaterials (2014) 35:630-641; Xie, et al., Acta Biomater. (2013) 9:5698-5707). PCL has shown degradability, hydrophobicity, good biocompatibility and high mechanical strength, resulting in FDA approval of many medical and drug application. PCL easily forms electrospun nanofibrous scaffolds with different natural and synthetic polymers (Gautam, et al., Mater. Sci. Engr. C (2013) 33:1228; Chaisri, et al., Biotech. J. (2013) 8:1323; Kim, et al., J. Nanomater. (2012) 2012:635212). Since the hydrophilicity increases the biocompatibility of materials, chitin, gelatin, silk protein and collagen have proven to have better biocompatibility (Kim, et al., J. Nanomater. (2012) 2012:635212; Zeybek, et al., Usak Univ. J. Mater. Sci. (2014) 3:121; Mandal et al., Biomaterials (2009) 30:2956; Fu, et al., Intl. J. Nanomed. (2014) 9:2335). Gelatin, which is non-water stable in conjunction with the synthetic polymers, is derived from hydrolyzed collagen. Compared to collagen, gelatin has good commercial reliability at a relatively low cost, but also has good compatibility and biodegradability (Maji, et al., Intl. J. Biomater. (2016) 9825659).

In order to prepare a highly hydrophilic 3D nanofibrous scaffold, 2D membranes were transformed into 3D nanofiber scaffolds using a modified gas-foaming technique (Jiang, et al. ACS Biomaterials Sci. & Eng. (2015) 1:991-1001; Jiang, et al., Adv. Healthcare Mater. (2016) 5:2993-3003; Jiang et al., Acta Biomater. (2018) 68: 237-248). Arrayed holes were punched throughout the 3D scaffolds. Human dermal fibroblast cell spheroids were prepared and seeded into the arrayed holes of 3D nanofiber scaffolds. The cell adhesion and migration were then examined in vitro. In terms of composition of scaffolds, a blend of PCL (a synthetic biodegradable and biocompatible polymer) and gelatin (a natural polymer), both approved by FDA for certain clinical applications (Kweon, et al., Biomaterials (2003) 24:801-808; Ungerleider, et al., Stem Cells Transl. Med. (2014) 3:1090-1099), was selected.

In accordance with the instant invention, nanofiber structures (sometimes referred to as scaffolds or nanofibrous herein) are provided. The nanofibers of the instant invention can be fabricated by any method. In a particular embodiment, the nanofiber structures comprise electrospun nanofibers. In a particular embodiment, the nanofiber structure comprises uniaxially aligned fibers, random fibers, and/or entangled fibers. While the application generally describes nanofiber (fibers having a diameter less than about 1 μm (e.g., average diameter)) structures and the synthesis of three-dimensional nanofibrous structures, the instant invention also encompasses microfiber (fibers having a diameter greater than about 1 μm (e.g., average diameter)) structures and the synthesis of three-dimensional microfibrous structures. In a particular embodiment, the nanofibrous structures are expanded, such as produced by a gas-foaming technique. For example, nanofiber structures (e.g., mats) may be expanded by being placed into conditions (e.g., submerged or immersed in a liquid) wherein gas bubbles are generated for various amounts of time. The nanofiber structure may be crosslinked (e.g., prior to expansion).

It is envisioned that the nanofiber scaffolds of the present invention can be formed and manufactured into a variety of shapes (ex. round, square, rectangular), sizes, and thicknesses. For example, the nanofiber structure may be cut or shaped prior to expansion. In one embodiment, the expanded nanofiber scaffold is from about 1 to about 20 mm thick. In another embodiment, the expanded nanofiber scaffold is from about 1 to about 10 mm thick. In another embodiment, the expanded nanofiber scaffold is from about 1 to about 5 mm thick.

The nanofibers of the instant invention may comprise any polymer. In a particular embodiment, the polymer is biocompatible. The polymer may be biodegradable or non-biodegradable. In a particular embodiment, the polymer is a biodegradable polymer. The polymer may by hydrophobic, hydrophilic, or amphiphilic. In a particular embodiment, the polymer is hydrophobic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyperbranched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: polyvinyl alcohol (PVA), poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(2-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly (tetrahydrofurane), ethyl cellulose, polydipyrolle/dicabazole, starch, polyvinylidene fluoride (PVDF), polytetrafluoroethylene (PTFE), polydioxanone (PDO), polyether poly (urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO. Amphiphilic copolymers may comprise a hydrophilic polymer (e.g., segment) and a hydrophobic polymer (e.g., segment) from those listed above (e.g., gelatin/PVA, PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/gelatin, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA). In a particular embodiment, the nanofiber comprises polymethacrylate, poly vinyl phenol, polyvinylchloride, cellulose, polyvinyl alcohol, polyacrylamide, PLGA, collagen, polycaprolactone, polyurethanes, polyvinyl fluoride, polyamide, silk, nylon, polybennzimidazole, polycarbonate, polyacrylonitrile, polyvinyl alcohol, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene gricol, polyethylene glycol, poly(ethylene-co-vinyl alcohol), polyacrylnitrile, polyvinyl pyrrolidone, polymetha-phenylene isophthalamide, gelatin, chitosan, starch, pectin, cellulose, methylcellulose, sodium polyacrylate, starch-acrylonitrile co-polymers, and/or combinations of two or more polymers. In a particular embodiment, the polymer comprises polycaprolactone (PCL). In a particular embodiment, the polymer comprises polycaprolactone (PCL) and gelatin (e.g., at a 1:1 ratio).

In a particular embodiment, the nanofiber structures comprise a material that enhances the nanofiber structure's ability to absorb fluids, particularly aqueous solutions (e.g., blood). In a particular embodiment, the nanofibers comprise a polymer and the material which enhances the absorption properties. In a particular embodiment, the nanofiber structures are coated with the material which enhances the absorption properties. The term "coat" refers to a layer of a substance/material on the surface of a structure. Coatings may, but need not, also impregnate the nanofiber structure. Further, while a coating may cover 100% of the nanofiber structure, a coating may also cover less than 100% of the surface of the nanofiber structure (e.g., at least about 75%, at least about 80%, at least about 85%, at least about 90%, at least about 95%, at least about 98%, or more the surface may be coated). Materials which enhance the absorption properties of the expanded nanofiber structures include, without limitation: gelatin, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the material is a hydrogel (e.g., a polymer matrix able to retain water, particularly large amounts of water, in a swollen state). In a particular embodiment, the material is gelatin. In a particular embodiment, the expanded nanofiber structures are coated with about 0.05% to about 10% coating material (e.g., gelatin), particularly about 0.1% to about 10% coating material (e.g., gelatin) or about 0.1% to about 1% coating material (e.g., gelatin). In a particular embodiment, the material (e.g., hydrogel) is crosslinked.

In a particular embodiment, the nanofiber structures of the instant invention are crosslinked. For example, the nanofiber structures of the instant invention may be crosslinked with a crosslinker such as, without limitation: formaldehyde, paraformaldehyde, acetaldehyde, glutaraldehyde, a photo-crosslinker, genipin, and natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132; incorporated herein by reference). The crosslinker may be a bifunctional, trifunctional, or multifunctional crosslinking reagent. In a particular embodiment, the crosslinker is glutaraldehyde.

As stated hereinabove, the nanofiber structures of the instant invention are expanded. Electrospun nanofibers are usually deposited on a substrate to form a nanofiber mat. However, the nanofiber mats are often dense and hard. These nanofiber mats can be expanded by making use of bubbles (e.g., generated by chemical reactions in an aqueous solution (e.g., a gas foaming technique)). The gas bubbles may be formed by any chemical reaction and/or physical mean. For example, the bubbles may be generated, without limitation, using a gas-production chemical reaction; by dissolved gas in a liquid under a high pressure and/or a low temperature; pressurized gas (e.g., $CO_2$) liquid; and/or physical means (e.g., laser (e.g., pulsed laser), acoustic induced, or flow induced). In a particular embodiment, the nanofiber structure is submerged or immersed in a bubble/gas producing chemical reaction or physical manipulation. Generally, the longer the exposure to the bubbles, the greater the thickness and porosity of the nanofiber structure increases. Examples of methods of expanding nanofiber structures are provided in PCT/US2015/052858 (incorporated herein by reference).

The gas bubbles of the instant invention can be made by any method known in the art. The bubbles may be generated, for example, by chemical reactions or by physical approaches. In a particular embodiment, the chemical reaction or physical manipulation does not damage or alter or does not substantially damage or alter the nanofibers (e.g., the nanofibers are inert within the chemical reaction and not chemically modified). As explained hereinabove, the nanofiber structure may be submerged or immersed in a liquid comprising the reagents of the bubble-generating chemical reaction. Examples of chemical reactions that generate bubbles include, without limitation:

$$NaBH_4 + 2H_2O = NaBO_2 + 4H_2$$

$$NaBH_4 + 4H_2O = 4H_2(g) + H_3BO_3 + NaOH$$

$$HCO_3^- + H^+ = CO_2 + H_2O$$

$$NH_4^+ + NO_2^- = N_2 + 2H_2O$$

$$H_2CO_3 = H_2O + CO_2$$

$$2H^+ + S^{2-} = H_2S$$

$$2H_2O_2 = O_2 + 2H_2O$$

$$3HNO_2 = 2NO + HNO_3 + H_2O$$

$$HO_2CCH_2COCH_2CO_2H = 2CO_2 + CH_3COCH_3$$

$$2H_2O_2 = 2H_2 + O_2$$

$$CaC_2 + H_2O = C_2H_2$$

$$Zn + 2HCl = H_2 + ZnCl_2$$

$$2KMnO_4 + 16HCl = 2KCl + 2MnCl_2 + H_2O + 5Cl_2$$

In a particular embodiment, the chemical reaction is the hydrolysis of $NaBH_4$ (e.g., $NaBH_4 + 2H_2O = NaBO_2 + 4H_2$). In a particular embodiment, $CO_2$ gas bubbles (generated chemically or physically (see below)) are used (e.g., for hydrophilic polymers).

Examples of physical approaches for generating bubbles of the instant invention include, without limitation: 1) create high pressure (fill gas)/heat in a sealed chamber and suddenly reduce pressure; 2) dissolve gas in liquid/water in high pressure and reduce pressure to release gas bubbles; 3) use supercritical fluids (reduce pressure) like supercritical $CO_2$; 4) use gas liquid (then reduce pressure) (e.g., liquid $CO_2$, liquid propane and isobutane); 5) fluid flow; 6) apply acoustic energy or ultrasound to liquid/water; 7) apply a laser (e.g., to a liquid or water); 8) boiling; 9) reduce pressure boiling (e.g., with ethanol); and 10) apply radiation (e.g., ionizing radiation on liquid or water). The nanofiber structure may be submerged or immersed in a liquid of the bubble-generating physical manipulation. The nanofiber structures of the instant invention may also be treated with air plasma prior to exposure to gas bubbles (e.g., to increase hydrophilicity).

Figure 6:
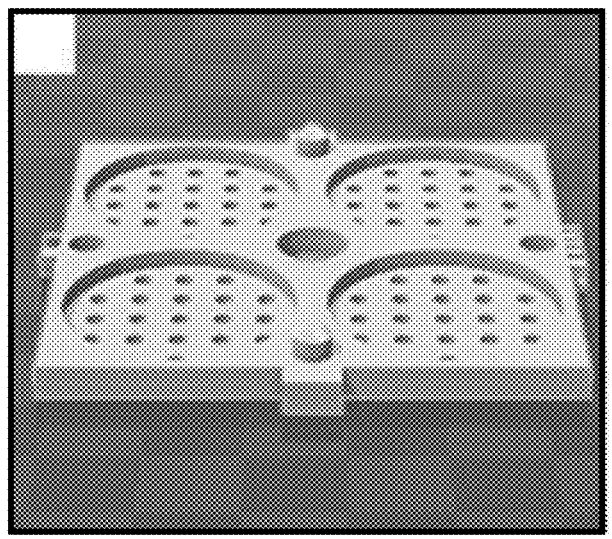
FIG. 6A provides the mold design.

The nanofiber structure may also be expanded within a mold (e.g., made of a metal, plastic, or other material that does not expand in the presence of gas bubbles) such that the expanded nanofiber structure forms a desired shape (e.g., pads, tubes, beads, etc.). In a particular embodiment, the mold is synthesized by a 3D printer. In a particular embodiment, the mold is as depicted in FIG. 6. The mold may contain holes that allow for punching corresponding holes in the nanofiber structure. The nanofiber structures of the instant invention may also be manipulated after expansion to form a desired shape (e.g., pads, tubes, beads, etc.).

As stated hereinabove, the nanofiber structures of the instant invention also comprise holes or wells. The wells/holes may be made in the nanofiber scaffold before or after expansion of the nanofiber scaffold. In a particular embodiment, the holes of the nanofiber structures are inserted prior to expansion. In a particular embodiment, the nanofiber structure is frozen (e.g., in liquid nitrogen) prior to insertion or punching of the holes. The holes of the nanofiber structure may be any shape (e.g., square, circle). The holes of the nanofiber structure can be any size. In a particular embodiment, the holes/wells have a length/dimension or diameter of about 0.1 to about 5 mm, particularly about 0.5 to about 3 mm or about 1.0 mm. The holes may be organized within the nanofiber structure in an array (e.g., a square array). In a particular embodiment, the holes of the nanofiber structure are generally equidistant from each other. The holes/wells of the nanofiber structures may all be the same size or may be various sizes. Any number of wells may be made in the nanofiber scaffolds. In one embodiment, the number of wells is between about 1 and about 200. The wells may be made using a variety of methods. In one embodiment, a mold with preset holes is used as a template to punch wells/holes into the nanofiber scaffold. The template may be made using a variety of techniques including but not limited to 3D printing.

After exposure to the bubbles, the nanofiber structure may be washed or rinsed in water and/or a desired carrier or buffer (e.g., a pharmaceutically or biologically acceptable carrier). Trapped gas bubbles may be removed by applying a vacuum to the nanofiber structure. For example, the expanded nanofiber structure may be submerged or immersed in a liquid (e.g., water and/or a desired carrier or buffer) and a vacuum may be applied to rapidly remove the gas bubbles. After expansion (e.g., after rinsing and removal of trapped gas), the nanofiber structures may be lyophilized and/or freeze-dried.

The nanofiber structures of the instant invention may also be sterilized. For example, the nanofiber structures can be chemically sterilized (e.g., by treating with ethylene oxide).

The holes/wells of the nanofiber structure of the instant invention may comprise cells or tissue. In a particular embodiment, the cells are autologous to the subject to be treated with the nanofiber structure. Any cell type can be added to the holes/wells. In a particular embodiment, the cells comprise stem cells. In a particular embodiment, the cells comprise dermal fibroblasts. In a particular embodiment, the holes/wells contain cell spheroids. In a particular embodiment, the holes/wells comprise tissue samples (e.g., minced tissue), such as skin tissue samples or bone samples. In a particular embodiment, the tissue samples have a length/dimension of diameter of about 0.1 to about 5 mm, particularly about 0.5 to about 3 mm or about 1.0 mm. The cells or tissue may be cultured with in the holes/wells of the nanofiber structure (e.g., the cells or tissue may be cultured for sufficient time to allow for infiltration into the nanofiber structure). For example, the cells or tissue may be cultured in the nanofiber structure for 1 day, 2 days, 3 days, 4 days, 5 days, or more.

The nanofiber structures of the instant invention may comprise or encapsulate at least one agent, particularly a bioactive agent such as a drug or therapeutic agent (e.g., analgesic, growth factor, anti-inflammatory, signaling molecule, cytokine, antimicrobial (e.g., antibacterial, antibiotic, antiviral, and/or antifungal), blood clotting agent, factor, or protein, etc.). The agent may be added to the nanofiber structures during synthesis and/or after synthesis. The agent may be conjugated to the nanofiber structure and/or coating material, encapsulated by the nanofiber structure, and/or coated on the nanofiber structure (e.g., with, underneath, and/or on top of the coating that enhances the nanofiber structure's ability to absorb fluids). In a particular embodiment, the agent is not directly conjugated to the nanofiber structure. In a particular embodiment, the agents are administered with but not incorporated into the expanded nanofiber structures.

In a particular embodiment, the agents enhance tissue regeneration, tissue growth, and wound healing (e.g., growth factors). In a particular embodiment, the agent treats/prevents infections (e.g., antimicrobials such as antibacterials, antivirals and/or antifungals). In a particular embodiment, the agent is an antimicrobial, particularly an antibacterial. In a particular embodiment, the agent enhances wound healing and/or enhances tissue regeneration (e.g., bone, tendon, cartilage, skin, nerve, and/or blood vessel). Such agents include, for example, growth factors and small molecules. Growth factors include, without limitation: platelet derived growth factor (PDGF), vascular endothelial growth factor (VEGF), epidermal growth factor (EGF), fibroblast growth factor (FGF, multiple isotypes; e.g. basic fibroblast growth factor (bFGF)), insulin-like growth factor (IGF-1 and/or IGF-2), bone morphogenetic protein (e.g., BMP-2, BMP-7, BMP-12, BMP-9), transforming growth factor (e.g., TGFβ, TGFβ3), nerve growth factor (NGF), neurotrophic factor, glial cell-derived neurotrophic factor (GDNF), and/or keratinocyte growth factor (KGF). Small molecules include, without limitation, simvastatin, kartogenin, retinoic acid, paclitaxel, vitamin D3, etc.

In accordance with another aspect of the instant invention, methods of synthesizing the nanofiber structures are provided. Generally, the method comprises electrospinning a nanofiber structure or mat, crosslinking the nanofiber structure or mat (optional), freezing (e.g., with liquid nitrogen) the nanofiber structure or mat (optional), inserting or punching holes into the nanofiber structure, expanding the nanofiber structure or mat with gas, washing and/or sterilizing the expanded nanofiber structure (optional), and seeding cells and/or tissue into the holes or wells of the expanded nanofiber structure. In a particular embodiment, the method further comprises plasma treatment of the nanofiber mat or structure prior to expansion. In a particular embodiment, the holes are punched into the nanofiber structure after gas expansion. In a particular embodiment, the method further comprises culturing the cells within the nanofiber structure (e.g., allowing the cells to infiltrate the nanofiber structure from the holes/wells).

The nanofiber structures of the instant invention can be used to create complex tissue architectures for a variety of application including, without limitation: wound healing, tissue engineering, tissue growth, tissue repair, tissue regeneration, and engineering 3D in vitro tissue models. The nanofiber structures can also be combined with a variety of hydrogels or biological matrices/cues to form 3D hybrid scaffolds that can release biologically functional molecules. The tissue constructs can be used for regeneration of many tissue defects (e.g., skin, bone) and healing of various wounds (e.g., injuries, diabetic wounds, venous ulcer, pressure ulcer, burns). The nanofiber structures may be used ex vivo to generate tissue or tissue constructs/models. The nanofiber structures may also be used in vivo in patients (e.g., human or animal) for the treatment of various diseases, disorders, and wounds. In a particular embodiment, the nanofiber structure stimulates the growth of existing tissue and/or repair of a wound or defect when applied in vivo. The nanofiber scaffolds can be used for engineering, growing, and/or regeneration of a variety of tissues including but not limited to skin, bone, cartilage, muscle, nervous tissue, and organs (or portions thereof).

In accordance with the instant invention, the nanofiber structures may be used in inducing and/or improving/enhancing wound healing and inducing and/or improving/enhancing tissue regeneration. The nanofiber structures of the present invention can be used for the treatment, inhibition, and/or prevention of any injury or wound. For example, the nanofiber structures can be used to induce, improve, or enhance wound healing associated with surgery (including non-elective (e.g., emergency) surgical procedures or elective surgical procedures). Elective surgical procedures include, without limitation: liver resection, partial nephrectomy, cholecystectomy, vascular suture line reinforcement and neurosurgical procedures. Non-elective surgical procedures include, without limitation: severe epistaxis, splenic injury, liver fracture, cavitary wounds, minor cuts, punctures, gunshot wounds, and shrapnel wounds. The nanofiber structures of the present invention can also be incorporated into delivery devices (e.g., a syringe) that allow for their injection/delivery directly into a desired location (e.g., a wound such as a gunshot wound). The nanofiber structures also may be delivered directly into a cavity (such as the peritoneal cavity) using a pressurized cannula.

In accordance with the instant invention, methods for inducing and/or improving/enhancing wound healing in a subject are also provided. Methods of inducing and/or improving/enhancing tissue regeneration (e.g., blood vessel growth, neural tissue regeneration, and bone regeneration) in a subject are also encompassed by the instant invention. The methods of the instant invention comprise administering or applying a nanofiber structure of the instant invention to the subject (e.g., at or in a wound). In a particular embodiment, the method comprises administering a nanofiber structure comprising an agent as described hereinabove. In a particular embodiment, the method comprises administering a nanofiber structure to the subject and an agent as described hereinabove (i.e., the agent is not contained within the nanofiber structure). When administered separately, the nanofiber structure may be administered simultaneously and/or sequentially with the agent. The methods may comprise the administration of one or more nanofiber structures. When more than one nanofiber structure is administered, the nanofiber structures may be administered simultaneously and/or sequentially.

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, an "anti-inflammatory agent" refers to compounds for the treatment or inhibition of inflammation. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 2,000). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. A "photocrosslinker" refers to a molecule capable of forming a covalent linkage between compounds after photoinduction (e.g., exposure to electromagnetic radiation in the visible and near-visible range). Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent.

The following examples are provided to illustrate certain embodiments of the invention. They are not intended to limit the invention in any way.

Example 1

Materials and Methods

PCL pellets (Mw=80,000) and gelatin powder of porcine skin were purchased from Sigma-Aldrich (St. Louis, Mo.). Hexafluoro-2-propanol (HFIP) was purchased from Oakwood Chemical, Inc. (Estill, S.C.). Glutaraldehyde in ethanol was bought from Ladd Research (Williston, Vt.). (3-(4,5-Dimethylthiazol-2-yl)-2,5-diphenyltetrazolium bromide) (MTT), Dulbecco's modified eagle medium (DMEM), and phosphate buffer saline (PBS) were obtained from Sigma-Aldrich (St. Louis, Mo.). Fetal bovine serum was obtained from Thermo Fisher Scientific (Waltham, Mass.).

Nanofiber mats were produced utilizing an electrospinning setup (Jiang, et al., ACS Biomaterials Sci. & Eng. (2015) 1:991-1001). The following parameters were used: 5% PCL and gelatin at a ratio of 1:1 (v/v) was electrospun at a flow rate of 0.4 mL/hour, a voltage of 18 kV, a spinneret (a 22-gage needle) and a drum (DC=20V for aligned fiber, and 3.5V for random fiber) located 20-23 cm away. The morphology of fiber samples was examined using scanning electron microscopy (SEM) (FEI, OR). In a sealed box, the PCL/gelatin nanofiber mats were cross-linked for 24 hours with glutaraldehyde vapor in ethanol at room temperature. To improve the hydrophilicity, plasma treatment (Harrick Plasma Inc., Ithaca, N.Y.) at medium radiofrequency (RF) level was used to treat PCL/gelatin nanofiber mats for 1 minute. The arrayed holes on the nanofiber mats were punched in liquid nitrogen. The nanofiber mats with arrayed holes were then expanded to form 3D scaffolds using a modified gas-foaming solution. In particular, a 1% $NaBH_4$ solution was used to prepare gas foamed electrospun 3D scaffolds. The nanofibrous mats were immersed in freshly prepared $NaBH_4$ solution at room ambient. The mats were gently rinsed 3 times with distilled water for 10 minutes each after 5-30 minutes gas foaming. $NaBH_4$ solution was discarded after dilution. The expanded 3D PCL/gelatin scaffolds were freeze-dried overnight. The scaffolds were sterilized with ethylene oxide prior to cell culture. The morphology of the nanofiber scaffold was examined using SEM. One drop of distilled water was added to the surface of fibers and kept for at least 5 minutes. The water stability of PCL/gelatin nanofibers before and after cross-linking was examined using SEM.

A hanging drop method was used to generate GFP-HDF cell spheroids (Foty, R., J. Vis. Exp. (2011) (51):2720; Fennema, et al., Trends Biotechn. (2013) 31:108-115). Each drop contained 20 µL of cell suspension the concentration of which was $10^6$ cells/mL. Cell spheroids of GFP-HDF were seeded to the surface of 2D PCL/gelatin scaffolds and the holes of 3D scaffolds. The samples were observed after 5 days of incubation. A fixative, which contains 2% glutaraldehyde and 2% paraformaldehyde in 0.1 M Sorensen's phosphate buffer (SPB), was used to fix the samples at 4° C. for overnight. The samples were washed 3 times using 0.1 M SPB and fixed using 1% osmium tetroxide solution for 30 minutes. The samples were washed with SPB and dehydrated in graded ethanol. Hexamethldisilazane (HMDS) solution was used to wash samples for 10 minutes and repeated for 3 times. The cell-seeded scaffolds were dried overnight. All the samples were fixed on a metallic stud with double-sided conductive tape and coated with platinum using a sputter coater. SEM images were acquired at an accelerating voltage of 15 kV.

The viability of GFP-HDF on nanofiber scaffolds was quantified using MTT assay. GFP-HDF was cultured in DMEM with 10% FBS at 37° C. in a 5% $CO_2$ incubator.

Before cell seeding, scaffolds were sterilized with ethylene oxide (EtO) for 12 hours. After sterilization, the scaffolds were incubated with PBS for 48 hours to obtain extracted solutions. Subsequently, the extraction (100 μL) of PCL, PCL/gelatin before crosslinking and PCL/gelatin after crosslinking were mixed with 100 μL fresh DMEM media and incubated in 96-well culture plate with GFP-HDF at a density of $10^5$ cell per well for 24 hours at 37° C. in 5% $CO_2$ incubator. After incubation, the wells were washed with PBS and then fresh complete media and MTT solution (5 mg/mL stock in PBS) were added at a ratio of 9:1 to the wells to make a final volume of 200 μL. The plate was then incubated at 37° C. for 4 hours. The media was discarded and 200 μL DMSO was added to the wells to dissolve the formazan crystals. The absorbance was measured using a Synergy™ H1 Hybrid Multi-Mode Microplate Reader (BioTek, Winooski, Vt.) at 490 nm. The relative growth rate (RGR) was defined as RGR (%)=(Absorbance of sample-Absorbance of blank/Absorbance of control)×100%. The cytotoxicity experiment was performed in triplicate (n=3) and the experimental results were presented as mean values±standard deviation (SD).

The 3D mold made of acrylonitrile butadiene styrene (ABS) was printed by a TAZ 5 3D printer (LulzBot, Loveland, Colo.).

Results

Figure 5:
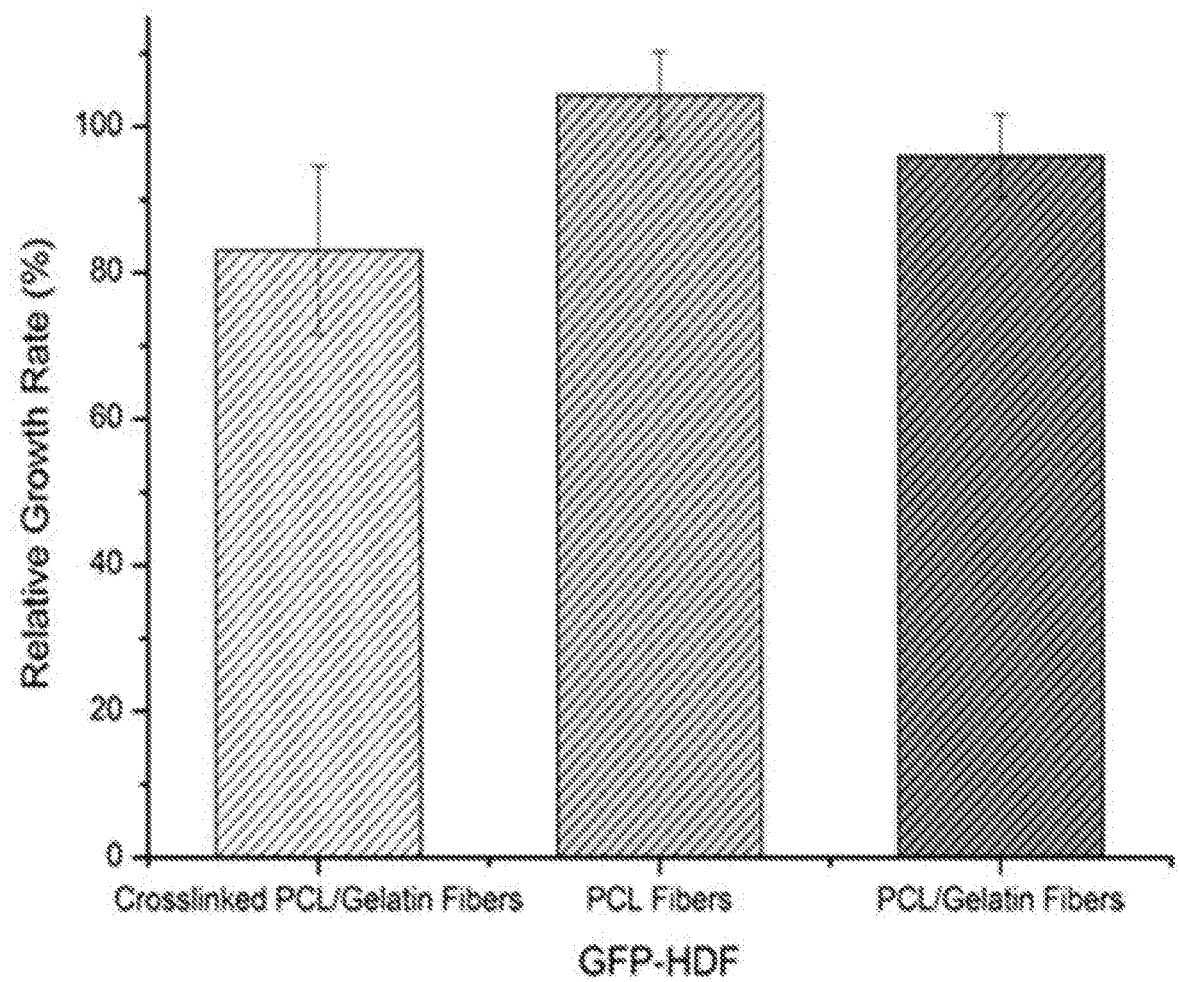
FIG. 5 provides a graph of the relative growth rates of green fluorescent protein-labeled human dermal fibroblasts (GFP-HDF) treated with extractions of electrospun scaffolds following ISO10993-5 tests (biological evaluation of medical devices) for in vitro cytotoxicity.

PCL/gelatin nanofibers were generated by electrospinning under different conditions (FIG. 2). It appears that the fiber diameter gradually became uniform with decreasing the PCL/gelatin concentration from 10% to 5% (w/v). The smooth and uniform fibers were obtained when the flow rate was 0.4 mL/hour and the PCL/gelatin concentration was 5% (w/v) (FIG. 2). By controlling rotating speed of the drum collector, aligned and random fibers were obtained (FIG. 3). The orientation of fibers was confirmed by a fast Fourier transform (FFT) analysis (FIG. 3). The gelatin is water soluble, necessitating crosslinking to preserve the fiber morphology in an aqueous environment. The glutaraldehyde vapor was used to crosslink PCL/gelatin nanofibers for maintaining their structural integrity since glutaraldehyde has been widely applied to covalently crosslink functional groups in natural polymers, such as gelatin and collagen (Kim, et al., Macromol. Biosci. (2010) 10:91-100). It is found that the fiber morphology of PCL/gelatin nanofibers was mainly preserved except for some minor swelling after water treatment (FIG. 4). To examine the potential cytotoxicity of cross-linked PCL/gelatin nanofibers, relative growth rates (RGR) of GFP-HDF were quantified when incubating with extractions of various fiber samples (FIG. 5). RGR of cross-linked and non-cross-linked PCL/gelatin nanofibers were higher than 80%, indicating a marginal cytotoxicity. To reduce the cytotoxicity even further, a more benign crosslinking method can be used such as photo-crosslinker, genipin or natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132).

Figure 7A:
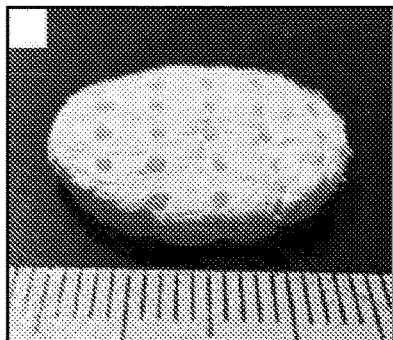
FIGS. 7A-7F provide the morphological characterizations of 3D PCL/gelatin (50:50) nanofiber scaffolds with arrayed holes.
Figure 7B:
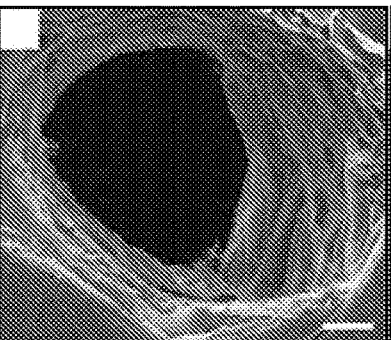
Figure 7C:
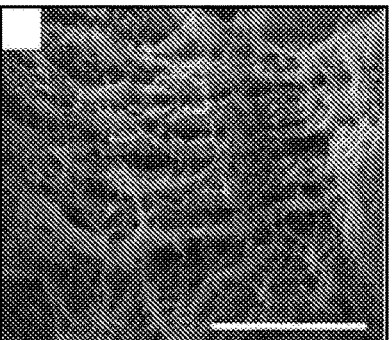
Figure 7D:
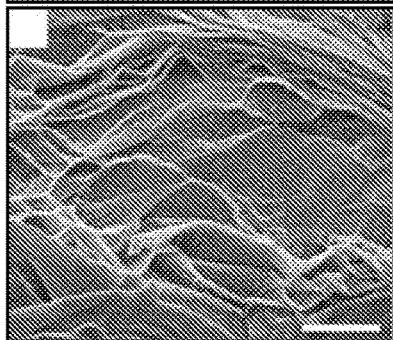
Figure 7E:
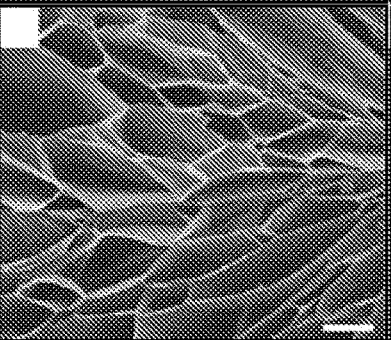
Figure 7F:
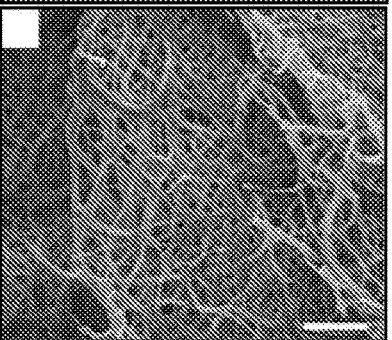

To form square arrayed holes throughout nanofiber membranes, membranes were first immersed into liquid nitrogen to make the materials brittle (below the glass transition temperature) and then created holes with a punch. Nanofiber membranes were expanded with square arrayed holes in a mold generated by 3D printer using a modified gas foaming technique (FIG. 6) (Jiang, et al., ACS Biomaterials Sci. & Eng. (2015) 1:991-1001; Jiang, et al., Adv. Healthcare Mater. (2016) 5:2993-3003). The nanofiber membrane was initially 0.4 mm thick and became about 4 mm thick after expansion. FIG. 7 shows the morphology of a 3D nanofiber scaffold with arrayed holes. As expected, the inner surface of punched holes displayed a layered structure (FIG. 7C). The SEM image of cross-sections indicated a layered and highly porous structure (FIGS. 7D-7F).

Figure 8A:
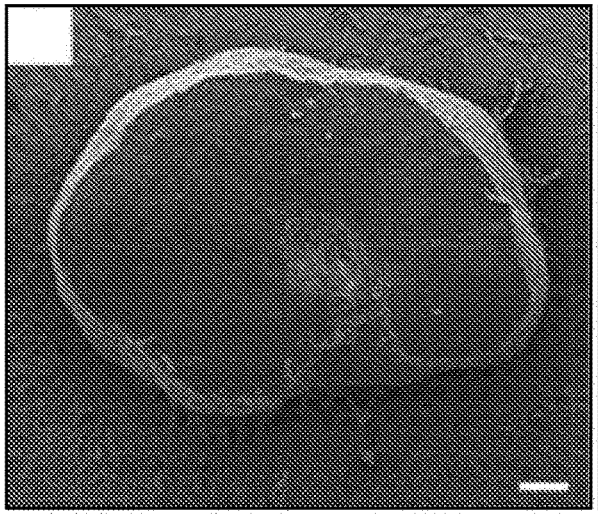
FIGS. 8A-8D provide images of cell spheroids-seeded 2D (FIGS. 8A, 8B) and 3D (FIGS. 8C, 8D) PCL/gelatin nanofiber scaffolds after incubation for 5 days. Scale bar=100 µm.
Figure 8B:
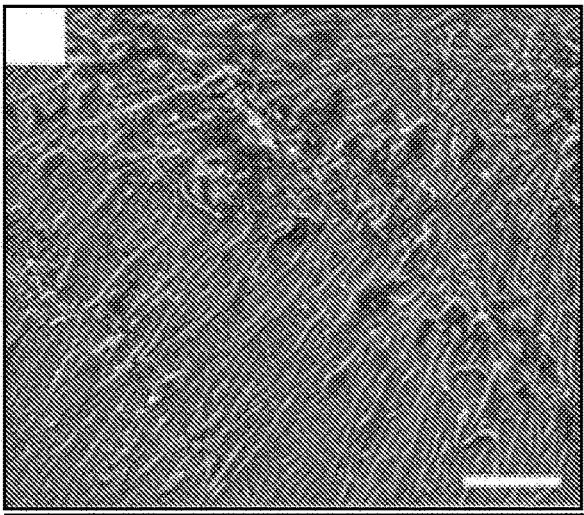
Figure 8C:
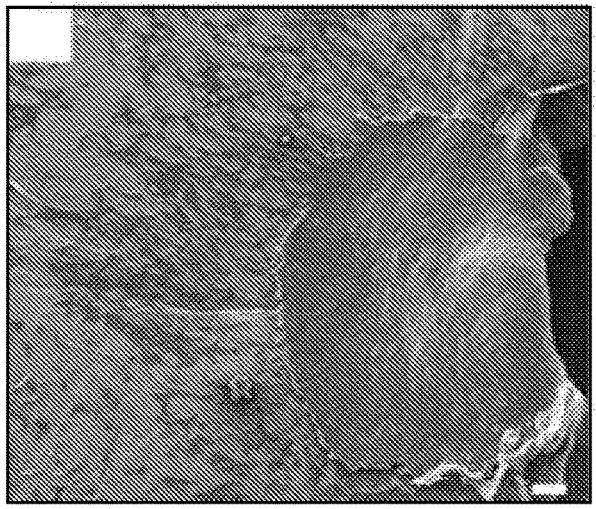
Figure 8D:
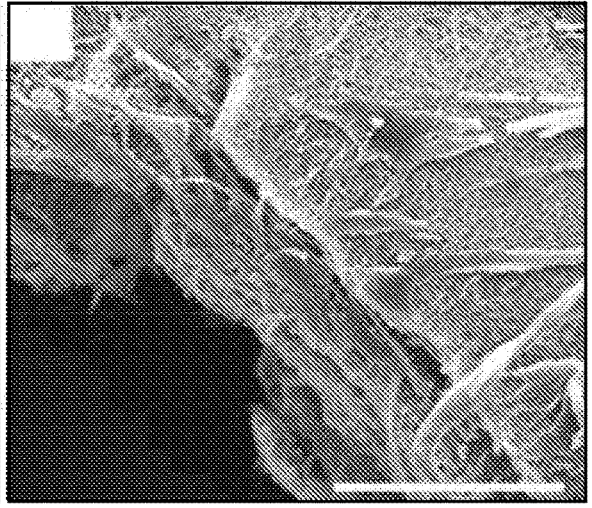

To demonstrate the proof-of-principle, GFP-HDF cell spheroids were prepared using a hanging drop method (Foty, R., J. Vis. Exp. (2011) (51):2720). An average diameter of 442.35±13.62 μm for cell spheroids was obtained after culture for 24 hours. Cell spheroids were seeded to the 2D and 3D nanofiber scaffolds. In order to prevent the falling of the cell spheroids, cell spheroids seeded on the scaffolds were immersed in a shallow level of cell culture medium overnight. After attached to the scaffolds, more cell culture medium was added to each well. After 5 days culture, it is observed that fibroblasts that were migrated from the cell spheroids seeded to 2D nanofiber membranes adhered and proliferated on the surface only (FIGS. 8A and 8B). In contrast, fibroblasts that were migrated from cell spheroids seeded into the holes of 3D nanofiber scaffolds adhered to the surface and surrounding nanofiber walls of holes (FIGS. 8C, 8D, and 9). Cells could further infiltrate into the scaffolds through the gaps between layers due to the layered and highly porous structures after expansion. The arrayed holes seeded with 3D cell spheroids showed a simultaneously cell infiltration and proliferation in three dimensions. It is expected that cells migrated from cell spheroids could infiltrate the surrounding space and form a 3D tissue construct. The plasma treated gelatin/PCL scaffolds showed better cell compatibility comparing with plasma-treated bare PCL scaffolds. All the cell spheroids have fallen off from the PCL scaffolds during the culture and material characterization. The cell migrated from the cell spheroids in 3D PCL/gelatin scaffolds and proliferated well on and in the scaffolds. Skin cells may migrate from the minced skin tissues seeded into the arrayed holes to the surrounding space and form 3D skin tissues for chronic wound closure.

To provide a promising skin tissue constructs, various methods of treatment have been suggested in the past, such as postage stamp grafting, mesh grafting, intermingled auto- and homograft transplantation, alternating strips of auto- and homograft transplantation, micro-skin grafting and the MEEK technique (Almodumeegh, et al., Intl. Wound J. I (2016) 1: doi: 10.1111/iwj.12650). The present 3D PCL/gelatin scaffolds further decrease the need of large donor sites. Moreover, the present 3D PCL/gelatin scaffold also provides physical protection and pain relief because of its hydrophilicity. The application of this 3D scaffolds with arrayed holes is ideal for wound treatment, both in chronic wound healing and acute wound healing such as 2nd degree and 3rd degree burns. Furthermore, the 3D cell spheroids had a comparable migration and proliferation of fibroblast comparing to typical 2D fibrous scaffolds.

Utilizing this approach, these 3D nanofiber scaffolds together with cell spheroids or minced tissues can create complex tissue architectures for wound healing, tissue regeneration, and engineering 3D in vitro tissue models (Cesarz, et al., Stem Cells Int. (2016) 9176357; Zanoni, et al., Sci. Rep. (2016) 6:19103). The scaffolds can also be combined with a variety of hydrogels or biological matrices/cues to form 3D hybrid scaffolds with eliciting biologically functional molecules (Chaisri, et al., Biotech. J. (2013) 8:1323; Franco, et al., J. Mater. Sci. Mater. Med. (2011) 22:2207; Manning, et al., Acta Biomater. (2013) 9:6905). The GFP-HDF can be changed to other cells, such as stem cells and cancer cells, which can produce extracellular matrix. The 3D scaffolds would biomimetic a physiological microenvironment with nanotopographic cues for hosting organotypic-like cell cultures. In addition, these novel 3D scaffolds with cost-effective fabrication could likely lead to the drastic change in the utilization of electrospun nanofibers.

A simple and reproducible approach to prepare 3D PCL/gelatin nanofiber scaffolds with arrayed holes has been provided. The cross-linking can significantly enhance the structural stability of nanofiber scaffolds in an aqueous environment. Seeded GFP-HDF spheroids displayed cell migration to the surface and surround nanofiber walls of punched holes. Combining 3D nanofiber scaffolds with arrayed holes and minced tissues is a promising strategy for chronic wound healing, regenerative medicine, as well as engineering in vitro tissue models.

Example 2

Figure 10D:
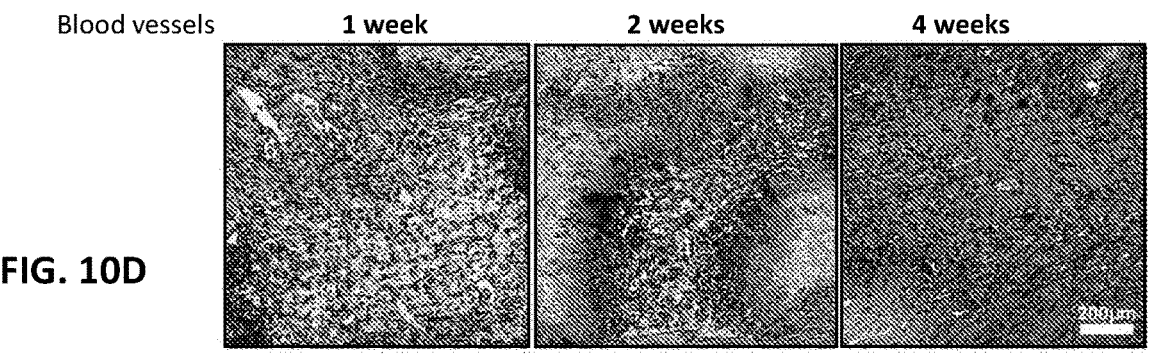
Figure 10E:
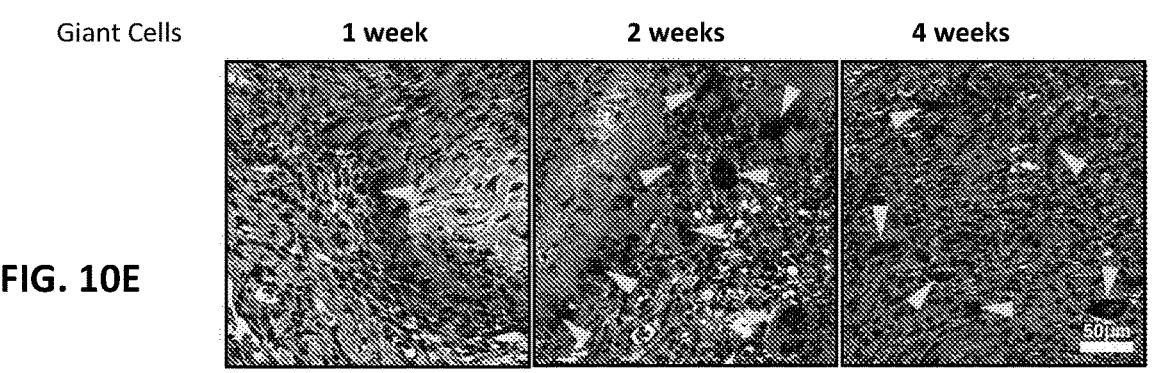
Figure 10F:
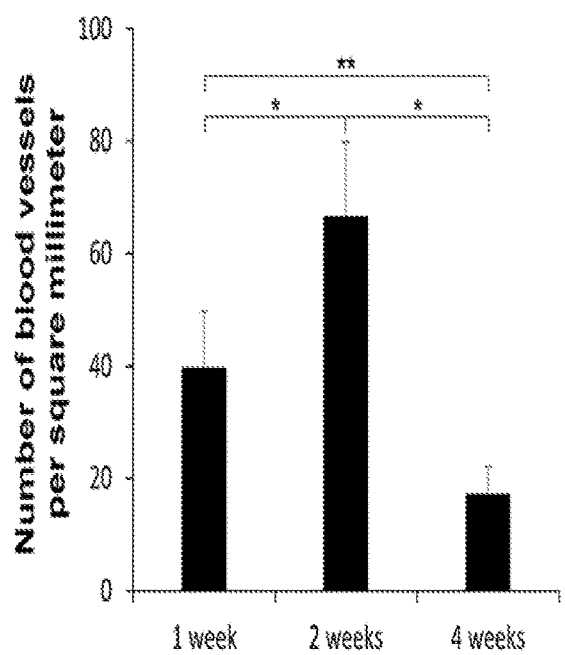
FIG. 10F provides a graph of the quantification of blood vessel formation per $mm^2$.
Figure 10G:
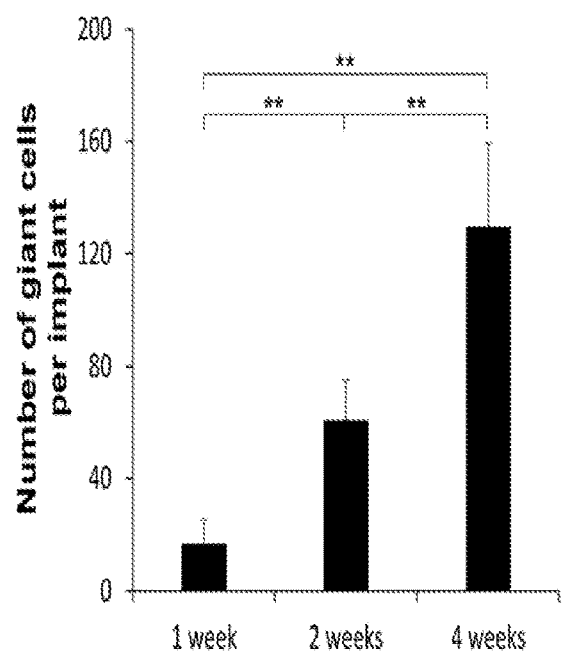
FIG. 10G provides a graph of the quantification of giant cells per implant.

To test the effect of expansion and punched holes on in vivo wound responses, the transformed PCL nanofiber scaffolds with arrayed holes were implanted subcutaneously in rats for 1 week, 2 weeks, and 4 weeks (FIG. 10A). Cells grew into the punched holes and then penetrated into the space between nanofiber thin layers within expanded nanofiber scaffolds (FIG. 10B). Masson trichrome staining shows the collagen deposition, indicated by arrows, from infiltrated cells in the punched holes and in the gaps between nanofiber thin layers (FIG. 10C). Many blood vessels were formed within the newly formed tissues in the holes or gaps between nanofiber layers (FIG. 10D). Multinucleated giant cells are also present (FIG. 10E). Numbers of blood vessels per $mm^2$ are approximately 40, 65, and 19 at week 1, 2 and 4, respectively (FIG. 10F). The presence of more blood vessels form at week 2 can be attributed to the early inflammatory response. Numbers of multinucleated giant cells per implant are 15, 50, and 140 at week 1, 2 and 4, respectively (FIG. 10G).

Figure 11:
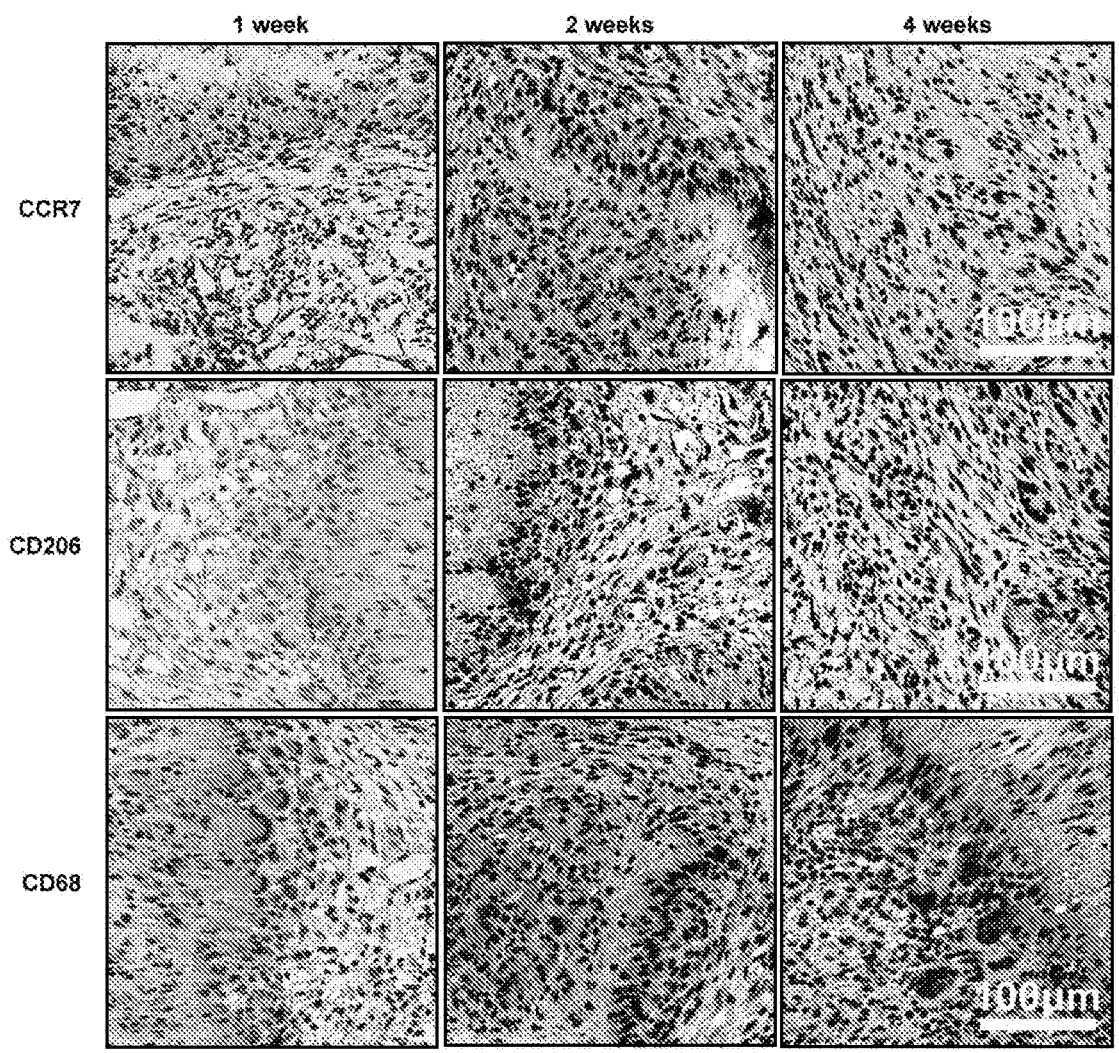
FIG. 11 provides images of immunohistological staining of PCL nanofiber scaffolds and surrounding tissues against CD68 (a surface marker for pan macrophages), CD206 (a surface marker for macrophages in M2 phase), and CCR7 (a surface marker for macrophages in M1 phase). The nanofiber scaffolds were subcutaneously implanted to rats for 1 week, 2 weeks, and 4 weeks.
Figure 12:
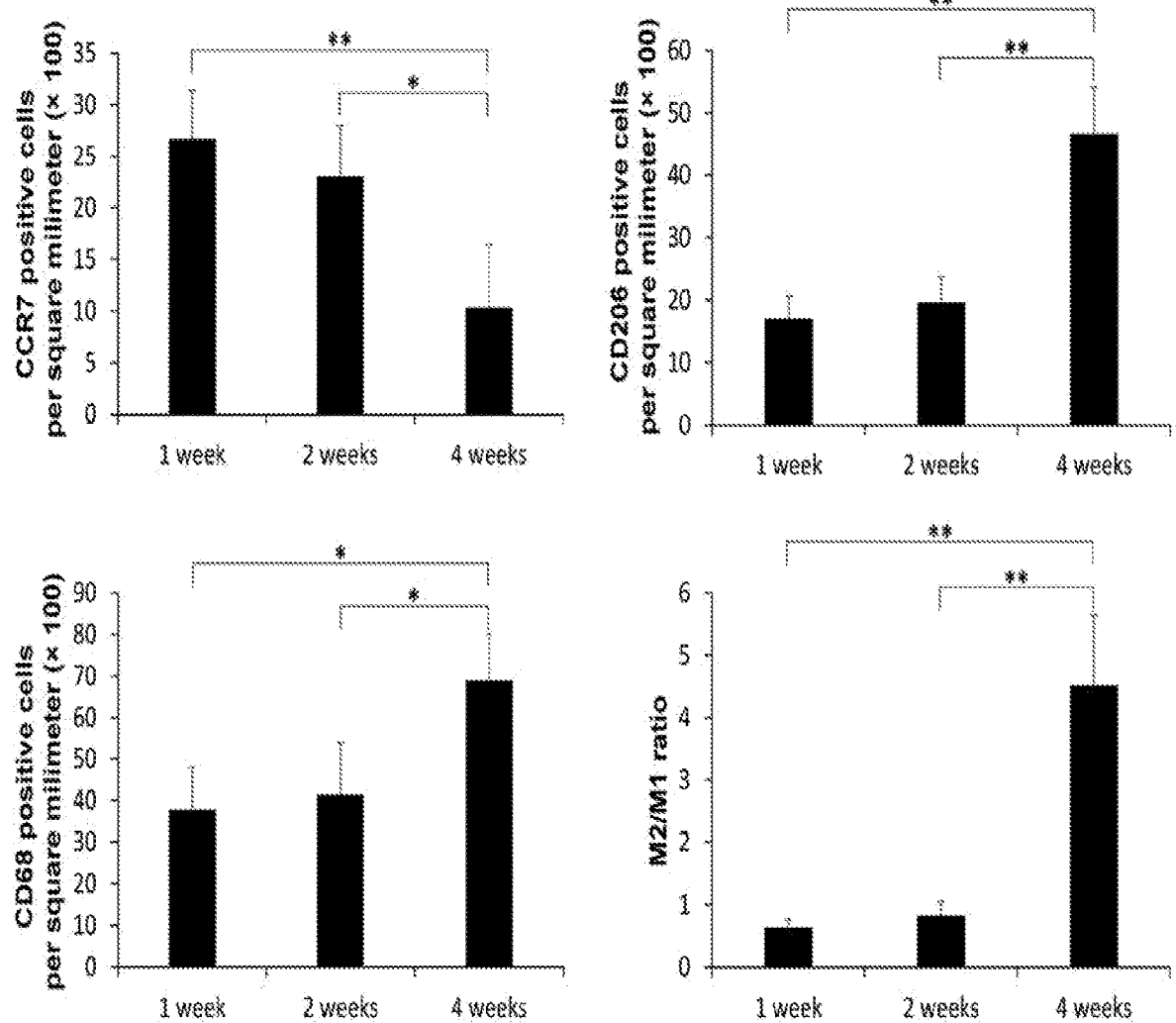
FIG. 12 provides graphs of the quantification of immunhistological analysis of PCL nanofiber scaffolds after subcutaneous implantation. The number of CD68, CCR7 (M1), and CD206 (M2) immunpositve cells are shown as well as the ratio of number of CD163 positive cells (M2)/number of CCR7 positive cells (M1). The values were obtained by measuring six scanning images at 40× (objective lens) magnification for each specimen.

Immunohistochemistry was then performed on PCL nanofiber scaffolds with punched holes and the surrounding tissues in order to identify infiltrated macrophages with different surface makers (FIG. 11). The number of CCR7 positive cells (macrophages in M1 phase which encourage inflammation) decreased while the number of CD206 positive cells (macrophages in M2 phase which decrease inflammation and encourage tissue repair) and CD68 positive cells (pan macrophages) increases with increasing implantation time. The quantified data for macrophages with different surface markers is shown in FIG. 12, indicating a dramatic increase of M2/M1 ratio at week 4 after implantation.

Figure 13:
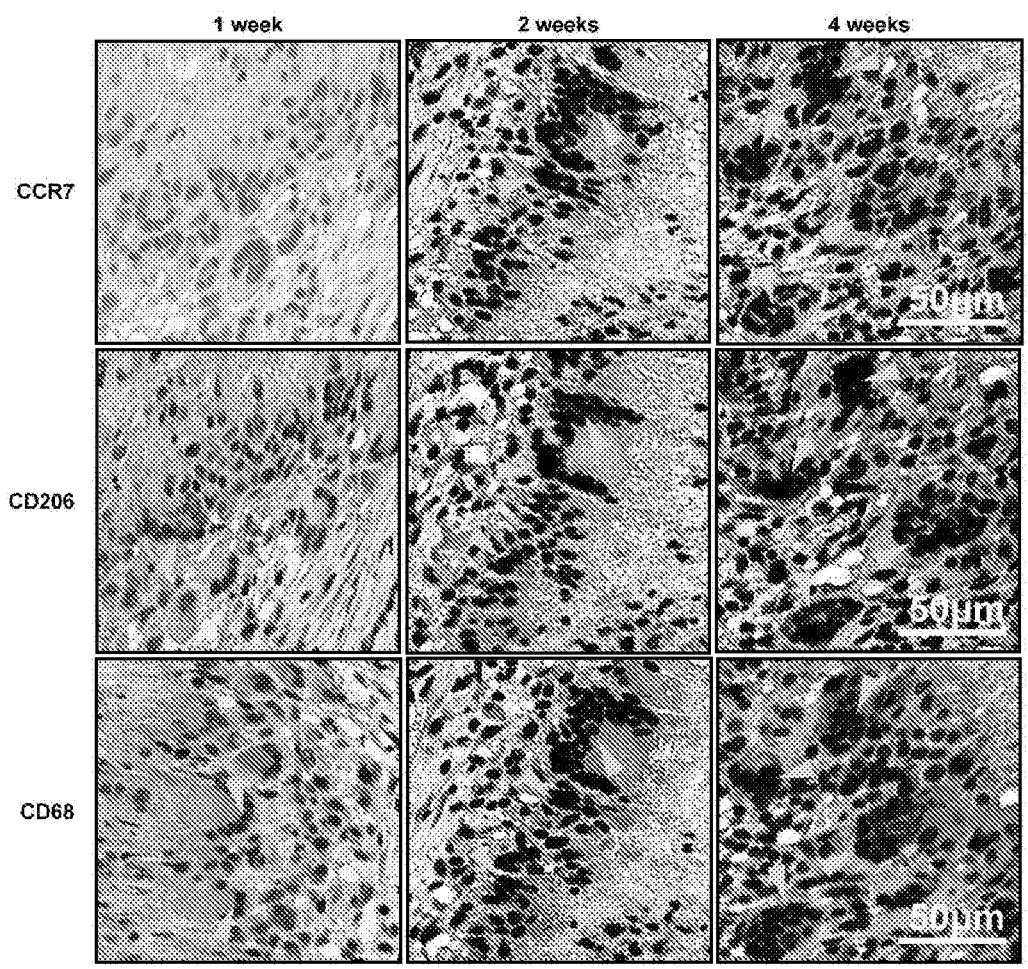
FIG. 13 provides images of multinucleated giant cells after nanofiber scaffold implantation. The rats were scarified at week 1, 2, and 4 after surgery. The multinucleated giant cells were stained against CD68, CD206, and CCR7. Arrows indicate multinucleated giant cells.

To reveal the expression markers and spatiotemporal distributions of multinucleate giant cells, immunohistochemistry with different surface markers was performed (FIG. 13). Notably, multinucleated giant cells are heterogeneous, expressing CCR7, CD206, and CD68 markers, can promote new blood vessel formation and tissue regeneration.

Figure 14:
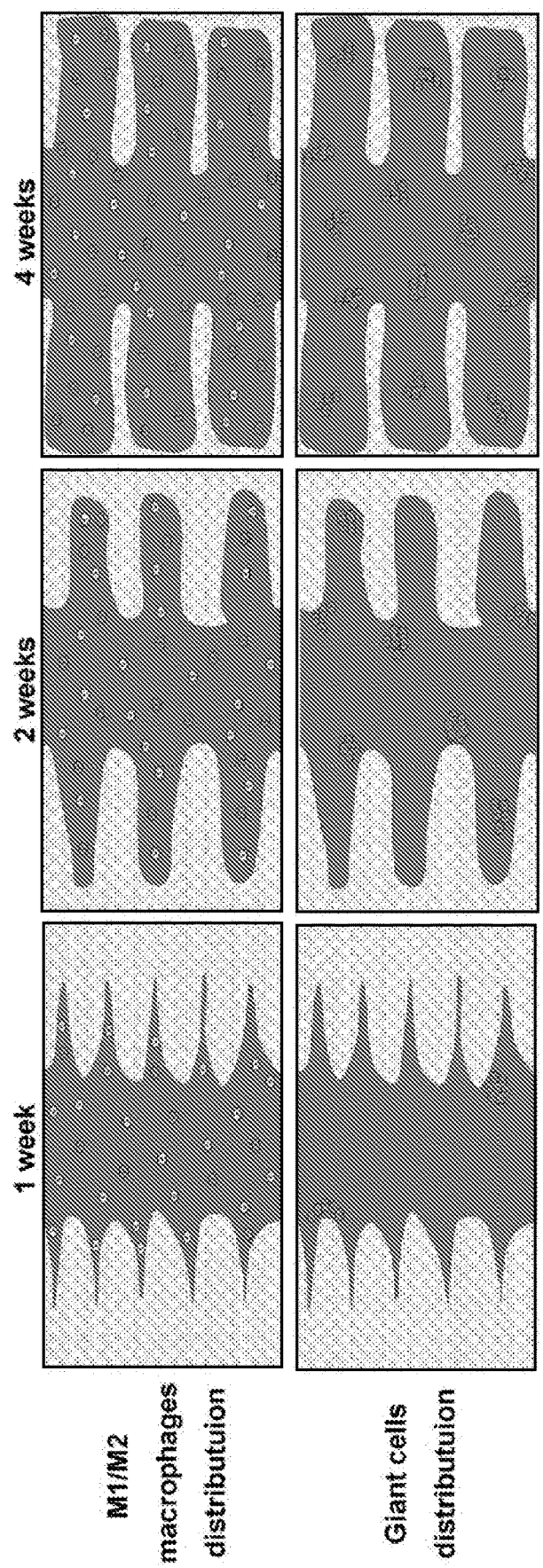
FIG. 14 provides a schematic illustrating the cell infiltration and spatiotemporal distributions of M1 macrophages (light grey), M2 (grey) macrophages (top panel) and multinucleated giant cells (bottom panel) within the 3D PCL nanofiber scaffolds after subcutaneous implantation. The cell-infiltrated area is labeled in dark grey.

Based on the immunostaining data, but without being bound by theory, cellular infiltration and spatiotemporal distributions of M1 macrophages, M2 macrophages, and multinucleated giant cells within the scaffold after implantation for 1, 2, and 4 weeks are proposed as seen in FIG. 14. Cells infiltrate into the punched holes within 1 week and continue penetrating to the scaffolds through the gaps between nanofiber layers. The macrophage infiltration shows the similar trend. There are more M1 macrophages at week 1 and 2 but more M2 macrophages at week 4. At week 1, multinucleated giant cells are mostly located on the surface of holes. At week 2, some giant cells are formed either on the surface of holes or on the infiltrated fiber layers. At week 4, multinucleated giant cells are relatively evenly distributed throughout the infiltrated areas.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An expanded, nanofibrous structure comprising electrospun nanofibers and an array of a plurality of holes.

2. The nanofibrous structure of claim 1, wherein said holes contain cells or tissue.

3. The nanofibrous structure of claim 1, comprising uniaxially-aligned nanofibers, random nanofibers, and/or entangled nanofibers.

4. The nanofibrous structure of claim 1, wherein said nanofibers comprise hydrophobic polymers.

5. The nanofibrous structure of claim 4, wherein said hydrophobic polymer is poly(caprolactone).

6. The nanofibrous structure of claim 1, wherein said nanofibers further comprise a material selected from the group consisting of gelatin, chitosan, starch, pectin, cellulose, methylcellulose, sodium polyacrylate, and starch-acrylonitrile co-polymers.

7. The nanofibrous structure of claim 6, wherein said nanofibers comprises gelatin.

8. The nanofibrous structure of claim 1, wherein said nanofibrous structure is crosslinked.

9. The nanofibrous structure of claim 1, further comprising a therapeutic agent.

10. The nanofibrous structure of claim 9, wherein said therapeutic agent is an anti-inflammatory, an antimicrobial, or a growth factor.

11. The nanofibrous structure of claim 2, wherein said cells or tissue comprise fibroblasts or stem cells.

12. The nanofibrous structure of claim 1, wherein said holes have a diameter of about 0.1 to about 5 mm.

13. The nanofibrous structure of claim 12, wherein said holes have a diameter of about 0.5 to about 3 mm.

14. The nanofibrous structure of claim 1, wherein said holes are generally equidistant from each other.

15. The nanofibrous structure of claim 1, wherein said holes are punched holes.

16. The nanofibrous structure of claim 1, wherein said holes traverse said nanofibrous structure.

17. The nanofibrous structure of claim 1, wherein said holes are all the same size.

18. The nanofibrous structure of claim 1, wherein said structure comprises 1 to about 200 holes in the array.

19. An expanded, nanofibrous structure comprising electrospun nanofibers and a plurality of punched holes.

20. The nanofibrous structure of claim 19, wherein said punched holes traverse said nanofibrous structure.

* * * * *